(12) United States Patent
Hibri

(10) Patent No.: US 10,881,522 B2
(45) Date of Patent: Jan. 5, 2021

(54) RADIALLY EXPANDABLE ANNULUS REINFORCEMENT PROSTHESIS

(71) Applicant: Nadi S Hibri, San Antonio, TX (US)

(72) Inventor: Nadi S Hibri, San Antonio, TX (US)

(*) Notice: Subject to any disclaimer, the term of this patent is extended or adjusted under 35 U.S.C. 154(b) by 707 days.

(21) Appl. No.: 15/428,918

(22) Filed: Feb. 9, 2017

(65) Prior Publication Data

US 2018/0221163 A1 Aug. 9, 2018

(51) Int. Cl.
*A61F 2/44* (2006.01)
*A61F 2/46* (2006.01)
*A61F 2/30* (2006.01)

(52) U.S. Cl.
CPC .......... *A61F 2/442* (2013.01); *A61F 2/4611* (2013.01); *A61F 2/30965* (2013.01); *A61F 2002/302* (2013.01); *A61F 2002/30069* (2013.01); *A61F 2002/30583* (2013.01); *A61F 2002/30586* (2013.01); *A61F 2002/30589* (2013.01); *A61F 2002/444* (2013.01); *A61F 2002/4435* (2013.01); *A61F 2002/4495* (2013.01); *A61F 2002/4627* (2013.01); *A61F 2002/4629* (2013.01)

(58) Field of Classification Search
CPC .................. A61F 2/442; A61F 2002/4435
See application file for complete search history.

(56) References Cited

U.S. PATENT DOCUMENTS

| 6,332,894 | B1* | 12/2001 | Stalcup | A61B 17/7097 623/17.11 |
| 6,371,990 | B1* | 4/2002 | Ferree | A61F 2/441 623/17.16 |
| 6,969,404 | B2* | 11/2005 | Ferree | A61B 17/1671 623/17.11 |
| 6,974,471 | B2 | 12/2005 | Van Schie et al. | |
| 7,442,210 | B2* | 10/2008 | Segal | A61F 2/441 606/279 |

(Continued)

*Primary Examiner* — Andrew Yang
(74) *Attorney, Agent, or Firm* — Gunn, Lee & Cave, P.C.; Robert L. McRae

(57) ABSTRACT

An intervertebral implantation system for restoring disc height and vertebral alignment, while allowing dynamic mobility and stabilization of the vertebral segment, and minimally invasive methods of implanting the same. The implantation system includes an annular reinforcement implant, including an elastomeric balloon inserted into the hollow or interior of a tubular sleeve, and secured only at a first and second neck portions to a securement element coupled to an attachment fixture, forming an annular structure attached to the outer margin of the annulus fibrosus. When the prosthetic implant is in a contracted state the tubular sleeve is redundant and undulated, forming folds, gathered loosely around the circumference of the inner balloon. Upon pressurized inflation with in-situ curable polymer, the elastomeric balloon elongates and expands circumferentially, and the tubular sleeve stretches and unfolds, constraining further expansion and elongation of the elastomeric balloon. The attachment fixture is configured to provide secure attachment to the outer margin of the annulus fibrosus. A temporary, high pressure vertebral distraction balloon is utilized to aid in vertebral distraction during a surgical procedure to implant the annular reinforcement implant.

22 Claims, 29 Drawing Sheets

(56) References Cited

U.S. PATENT DOCUMENTS

| | | | | |
|---|---|---|---|---|
| 7,547,319 B2* | 6/2009 | Segal | ............... | A61F 2/441 |
| | | | | 606/246 |
| 8,636,803 B2* | 1/2014 | Hibri | ............... | A61F 2/441 |
| | | | | 623/17.12 |
| 2004/0097927 A1* | 5/2004 | Yeung | ............... | A61B 17/1757 |
| | | | | 606/86 A |
| 2006/0293749 A1* | 12/2006 | Hudgins | ............... | A61F 2/441 |
| | | | | 623/17.11 |
| 2009/0112323 A1* | 4/2009 | Hestad | ............... | A61F 2/441 |
| | | | | 623/17.12 |

* cited by examiner

RADIALLY EXPANDABLE ANNULUS REINFORCEMENT PROSTHESIS

BACKGROUND

1. Field of the Invention

The present invention generally relates to an annular expandable intervertebral disc prosthesis. More particularly, the present invention relates to a prosthetic graft structure which can be inflated in-situ to form an implant useful for supporting a damaged or torn annulus fibrosus, and for correction of deformity associated with adult degenerative lumbar scoliosis (ADLS) and degenerative disc disease (DDD).

2. Background

Tubular prostheses are commonly used in various vascular grafting applications. Implantable tubular endoprostheses such as stent-grafts and other similar devices are well known in the art for the treatment of various bodily lumens, such as the gastrointestinal system, the airway, and other applications in the body. The tubular configuration and design of such prostheses is desirable because these prostheses have characteristics which attempt to resemble the body lumen which it is supporting.

Many devices have been invented for the purpose of stabilizing the vertebral segment and/or replacing parts of the intervertebral disc in an effort to ease pain associated with disc disease. Included amongst the latest of such devices are expandable bags or balloons that are initially flexible but become turgid with materials that can support loads. As such, these latest devices are intended to function as nucleus pulposus replacement, and aim to preserve normal motion. Other devices known in the art are essentially improved inter-body fusion devices. In general, prior art prostheses have limitations in their compliance properties, compactness, and foldability. Another disadvantage of presently available intradiscal devices is that they lack radial and longitudinal compliance, and are too rigid or stiff. As such, they lacked characteristics which closely resemble those of a normal intervertebral disc or those of the nucleus pulposus, or annulus fibrosus which they are replacing.

A notable challenge encountered in prior art designs of prostheses intended for intradiscal implantation is to maintain compliance, elasticity, collapsibility, and flexibility of the prosthesis. Furthermore, grafts utilized lacked resilience and durability. Intradiscal implants undergo intermittent loading in response to axial and torsional forces. As a consequence, an implant must be able to withstand fatigue. Kinking resistance is also a desirable feature when compressing a graft/implant during the loading operation in a delivery instrument and when inflating or expanding the prosthesis during the procedure. Matching the synergistic compliance of the graft and the Young's modulus of elasticity of the material inflating its lumen with the viscoelastic properties is one of the most important requirements for long term success of an intradiscal implant.

The current invention represents departure from previous prior art and aims to particularly address what is believed to be at the core of the accelerated degenerative and/or deformity cascade of the lumbar spinal segment leading to pain and deformity, namely, radial tear of the annulus fibrosus. With the associated loss of intradiscal pressure, loads are transferred to the annulus of the disc and to the facet joints of the associated vertebrae. These latter structures are not capable of withstanding the applied compression and torsional loads and they gradually deteriorate. Some patients develop accelerated DDD, others develop ADLS, which may become symptomatic. "Segmental instability" is believed to be integral to this process.

Accordingly, it is desirable to provide a new and improved implantable intervertebral disc implant which is annular in configuration and serves to reinforce a defective annulus fibrosus, and is useful in the treatment of ADLS and DDD. Unlike prior art prostheses that are tubular, the elastomeric implant of the present invention is annular in configuration with characteristics closely resembling those of a natural annulus fibrosus. The annular configuration of the present invention overcomes the issues and difficulties associated with conventional tubular or cylindrical endoprostheses due to the differences in design and manufacturing of implants of the present invention that allows them to perform as intended. The elastomeric implant of the present invention is compliant to axial and torsional loads. The compliance of the present invention is accomplished by providing space between the outer surface of an inner elastomeric layer and the inner surface of an outer semi-compliant tubular braid or sleeve. Thus, the layers can move independently and this obviates the problem of compliance mismatch between the two layers of the implant.

The implant of the present invention is delivered to the disc space loaded in a collapsed state in a delivery cannula, and deployed percutaneously or by minimally invasive surgical procedures. The graft component is annular in configuration and elongates circumferentially and expands radially outwards to augment a torn or weakened annulus. Simultaneously, it expands axially to exert pressure against the vertebral end plates to restore disc height and normal angulation, share load with the intrinsic annulus, stabilize the vertebral segment, and ease pain while preserving normal motion.

SUMMARY OF THE INVENTION

The present invention provides an intervertebral annular reinforcement implant with a delivery and deployment system and an attachment system and methods for their use in repairing a damaged intervertebral disc. The prosthetic implant is made of elastomeric materials, and is inflatable and expandable within the disc space of a patient with ADLS or DDD, and is designed to repair a deteriorating or torn annulus fibrosus and restore disc height and vertebral alignment, while allowing dynamic mobility and dynamic stabilization of the vertebral segment.

The delivery and deployment system is configured to introduce a deflated and contracted prosthetic implant into the disc space of an animal such as a human by minimally invasive surgical methods, to facilitate appropriate placement of the prosthetic implant along the inner margin of the annulus fibrosus prior to inflation. After proper placement, the delivery and deployment system inflates the prosthetic implant with in-situ curable elastomer, pressurizes the implant differentially to widen the disc space, thereby restoring vertebral alignment, and stabilizing the vertebral segment.

In one illustrative embodiment, the present invention is directed to a prosthetic implant including an outer tubular textile sleeve which is hollow, and encloses an inner elastomeric balloon therein extending along its length. The elastomeric balloon and the tubular textile sleeve are preferably separate and distinct, and are free to move independently with respect to one another, and are secured to an securement element stationed along the outer margin of the annulus fibrosus only at a first neck portion and a second neck portion of the tubular sleeve.

Another illustrative embodiment of the present invention is directed to the securement element configured to bond the first and second neck portions of the tubular sleeve and elastomeric balloon to a polymeric insert component of the securement element. The first neck portion of the elastomeric balloon is further sealably bonded to a fluid coupling apparatus and a valve in the securement element. The second neck portions of the tubular sleeve and elastomeric balloon are sealed or tied to the polymeric insert, thus forming an annular, inflatable and expandable elastomeric structure.

Another illustrative embodiment of the present invention includes an access cannula inserted into the annulus fibrosus with its tip in the disc space preferably by minimally invasive surgical procedure. The delivery and deployment system of the invention is slidable within the access cannula to gain access to the disc space. The delivery and deployment system includes a rigid delivery cannula having distal and proximal ends, and a lumen extending therebetween. The distal end of the delivery cannula has a loading portion housing the prosthetic implant in a contracted state. The prosthetic implant is coupled to an inflation cannula, a disengagement implement, an attachment apparatus, and a pusher element. In one embodiment, a high-pressure balloon is included in the space interior the annular prosthetic implant.

In another illustrative embodiment of the present invention, the temporary high-pressure balloon is loaded in the delivery cannula in conjunction with the prosthetic implant. The high-pressure balloon resides at the center of the annular prosthetic implant, interior to the elastomeric balloon, and is configured to aid in distraction of the adjacent vertebrae. Furthermore, the high-pressure balloon, when inflated, aids in advantageously displacing the prosthetic implant towards the outer margin of the disc space.

In another illustrative embodiment of the present invention, a method of implanting the prosthetic implant within the disc space of a patient is provided. The method includes accessing the disc space by methods known by those skilled in the art, preferably using minimally invasive surgical technique, introducing the delivery cannula of the present invention through the access cannula, advancing the inflation cannula, disengagement implement, and pusher implement in unison to deploy the prosthetic implant into the disc space, controllably inflating the elastomeric balloon with liquid in-situ curable polymer and temporary high-pressure balloon with contrast material, differentially expanding the prosthetic component to widen the disc space and correct segmental deformity, allowing the in-situ curable polymer to cure within the implant (thus reinforcing the defective or torn annulus fibrosus), and deflating and moving the high-pressure balloon.

In yet another illustrative embodiment of the present invention, a method of attaching the attaching fixture to the outer margin of the annulus fibrosus is described. The method includes retracting the access cannula to a level immediately outside the annulus fibrosus, allowing the annulus fibrosus aperture to contract, aligning the tip of the delivery cannula in close proximity to the outer annulus margin, driving the pusher implement forward against an attachment ring, urging a plurality of staple legs to penetrate the annulus and securely affix or anchor the prosthetic implant to the native annulus.

In yet another illustrative embodiment of the present invention, a method of disengaging the prosthetic implant from the inflation cannula is provided. The method includes exerting forward pressure on the inflation cannula and pusher element, while applying a steady pulling force on the inflation cannula to achieve atraumatic disengagement. As the inflation cannula is retracted, the valve contracts to form a slit, providing fluid-tight sealing of the elastomeric balloon.

DESCRIPTION OF THE DRAWINGS

FIG. 10A is a fragmentary cross-sectional view of a securement element of one embodiment of the present invention, positioned within the distal lumen of a delivery cannula, showing the relationship of the first and second neck portions of the annular component to the securement element, following partial inflation of the annular lumen with liquid silicone.

FIG. 14H is a sectional view similar to FIG. 15G taken following insertion of a loaded delivery cannula through the access cannula.

DETAILED DESCRIPTION

Turning now to the Figures, reference numbers are used to designate corresponding elements in the Figures. The Figures depict selected embodiments. Although the present invention will be described with reference to preferred embodiments, those skilled in the art will recognize that changes may be made in form and detail without departing from the scope and spirit of the invention. Examples of construction, materials, dimensions, and manufacturing process are provided. It is intended that the following detailed specification be regarded as illustrative rather than limiting, and it is the appended claims, including all equivalents thereof, which are intended to define the scope of the invention.

Figure 1:
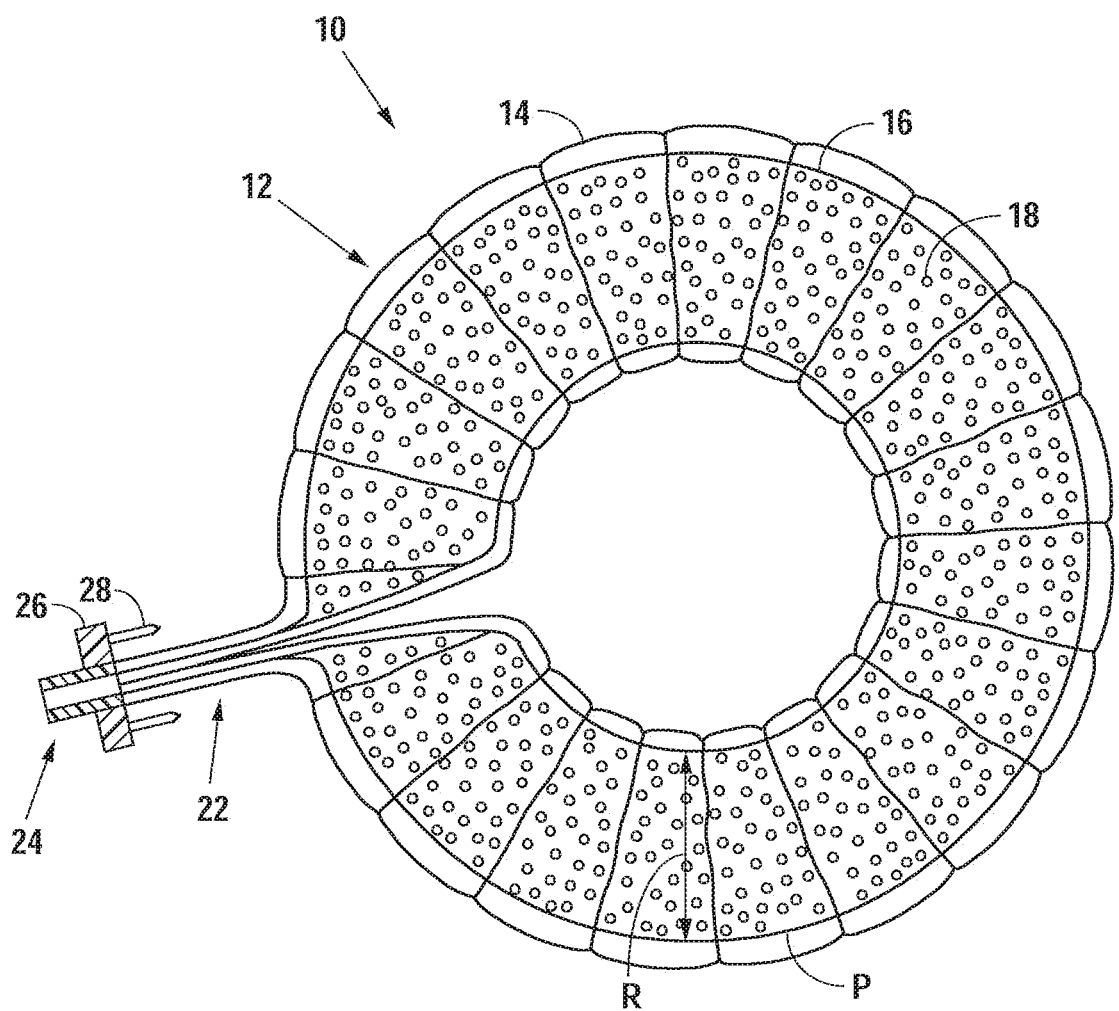
FIG. 1 is a partial cross-sectional top view of an annular prosthetic implant in accordance with one embodiment of the invention.
Figure 2A:
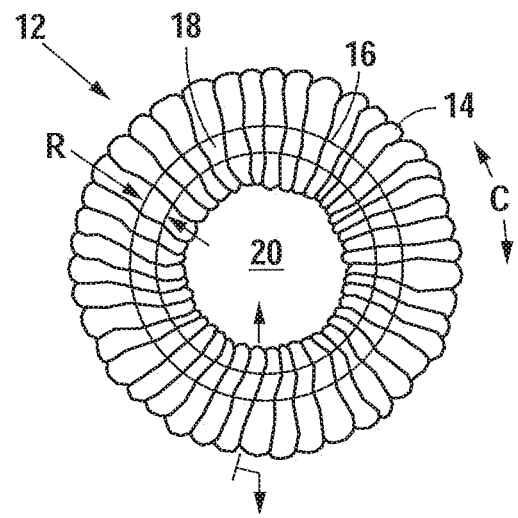
FIG. 2A is a partial cross-sectional top view of an annular prosthetic implant with the elastomeric balloon uninflated.
Figure 2B:
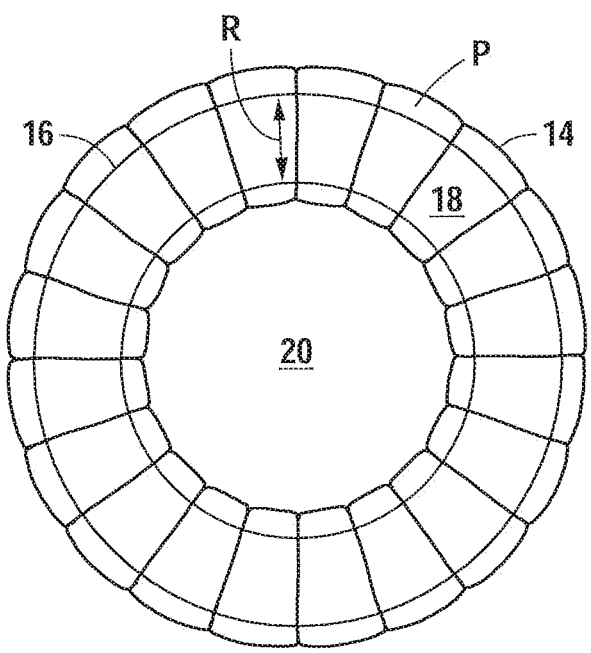
FIG. 2B is a partial cross-sectional top view of an annular prosthetic implant with the elastomeric balloon inflated.

Referring now to FIG. 1, there is shown an embodiment of an intervertebral elastomeric device 10. The device 10 comprises an annular component 12 which comprises an annular balloon 16 formed in the shape of an annular membrane, and a textile supporting sleeve 14 positioned about the outer circumference of the annular balloon 16. Referring to FIGS. 2A and 2B, the annular component 12 has a first compact non-inflated configuration that facilitates packing in a minimal profile within a delivery cannula 56 (see FIG. 13) configured for percutaneous or minimally invasive deployment, and a second expanded configuration (shone in FIG. 2B) following in-situ inflation of its annular lumen 18 with curable liquid elastomer such as RTV "room temperature vulcanizing" medical grade silicone. The annular component 12 expands in the circumferential and radial directions as indicated by the arrows C and R, respectively.

Figure 4A:
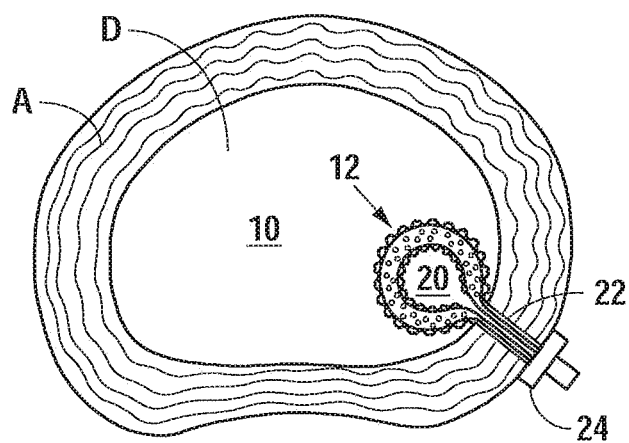
FIGS. 4A, B and C are partial cross-sectional top views of an annular prosthetic implant demonstrating incremental inflation of the elastomeric balloon and expansion of the prosthetic implant within the disc space.

Referring now to FIG. 1, and FIGS. 4A, B, C, the annular balloon 16 and the overlying textile supporting sleeve 14 assume an annular configuration with the annular balloon 16 having two mouth portions 16a and 16b that converge at a neck portion 22 that is coupled to a securement element 24. When the annular component 12 is deployed and inflated in an intervertebral disc space D, the neck portion 22 is constrained by the aperture created in the annulus fibrosus A and the securement element 24 is affixed to the outer margin of the annulus fibrosus A.

The term "balloon" is used broadly throughout this disclosure to refer to a variety of inflatable medical devices having a variety of shapes, characteristics, and uses. The term "annular balloon" is used specifically throughout this disclosure to refer to a tubular elastomeric membrane, formed into an annular configuration comprising a wall defining an annular lumen 18 of the annular balloon 16, and separating the annular lumen 18 from the external environment when one or both ends of the annular balloon 16 are sealed. When the annular lumen 18 is completely empty the wall of the annular balloon 16 assumes a minimal flexible profile and the textile supporting sleeve 14 is flexible and redundant, forming creases and folds as shown in FIGS. 1, 2A, and 2B. When collapsed, the annular component 12 may be stretched in a direction away from the securement element 24 and can be elastically deformed to reduce its diameter with some degree of elongation, into a minimal profile to fit within a delivery cannula 56.

Referring again to FIG. 1, the annular balloon 16 and the textile supporting sleeve 14 are separate and unbonded, and are free to move independently along the entire annular circumference of the annular component 12 with a potential space P therebetween. The annular balloon 16 may be formed of a variety of elastomeric materials well known in the art including silicone, nylon, PEBAX, or any thermoplastic material. Multilayered balloons may be comprised of multiple layers of the same material, or layers of different materials. In one embodiment, the annular balloon 16 is compliant, to provide optimal elongation and inflation capability, and is formed of silicone by a dispersion dipping process, injection molding, or other manufacturing techniques known in the art. The annular balloon 16 has a wall thickness prior to expansion ranging from 0.05-1.02 mm. The annular component comprises the annular balloon 16 which defined potential space P and the textile supporting sleeve 14. In one embodiment, the annular component 12 is formed of a fabric reinforced silicone material to possess a soft yet semi-compliant structural disposition. The fabric layer may represent an electrospun polymeric component having some degree of penetration of the silicone component onto the pores of the fabric polymeric component.

Figure 3A:
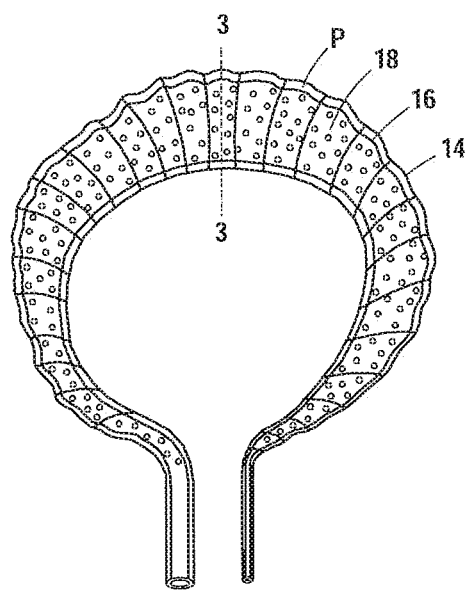
FIG. 3A is a partial cross-sectional top view of an annular prosthetic implant with the elastomeric balloon partially filled with in situ-curable polymer and the implant is in its annular configuration.
Figure 3B:
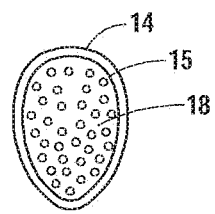
FIG. 3B is a cross sectional view of the annular prosthetic implant along line 3-3 of FIG. 3A with the elastomeric balloon inflated.
Figure 3C:
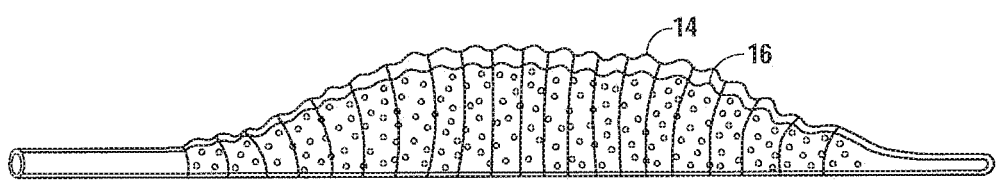
FIG. 3C is a partial cross section view along of the annular prosthetic implant, along line 3-3 of FIG. 3A with the elastomeric balloon partially filled with in situ-curable polymer and the implant in its straightened configuration.

Referring to FIGS. 3A, B and C, the annular component 12 may have a crescentic configuration whereby the cross-sectional diameter of the annular component 12 tapers toward the firs neck portion 22a and second neck portion 22b. The relatively wide mid-section of the annular component 12, contralateral to the position of the securement element 24, is configured to provide augmentation to a relatively weakened or disrupted annulus fibrosis in this region as will be demonstrated in more detail hereinafter.

In one embodiment, the annular balloon 16 has a rated burst pressure of at least 15 atmospheres, and exhibits a compliance of 0.5% expansion per atm. to about 1.5% expansion per atm. in a radial direction when pressurized from a fully inflated volume to the rated pressure of the balloon. Typically, the annular balloon 16 can have an inflated diameter between 15-15 mm, with a tapered neck portion that can fit over and be bonded to the valve base 54, preferably by a silicone adhesive, heat bonding, or UV curing may also be utilized. The annular balloon 16 shown in FIG. 1 inflates uniformly so that it remains concentric with respect to the textile supporting sleeve 14, without off-side, non-uniform, or irregular expansion. Different compliant balloon lengths and diameters can be readily utilized as needed. The textile supporting sleeve 14 works to constrain annular balloon 16. Also, the composition, durometer, wall thickness, and other physical characteristics can be tailored to guard against inadvertent rupture. The annular balloon 16 may be noncompliant. Annular balloons of relatively high tensile strength can be formulated. The annular balloon 16 may be formed by molding methods known to those skilled in the art, including dip molding, injection molding, and extrusion molding techniques.

Figure 5A:
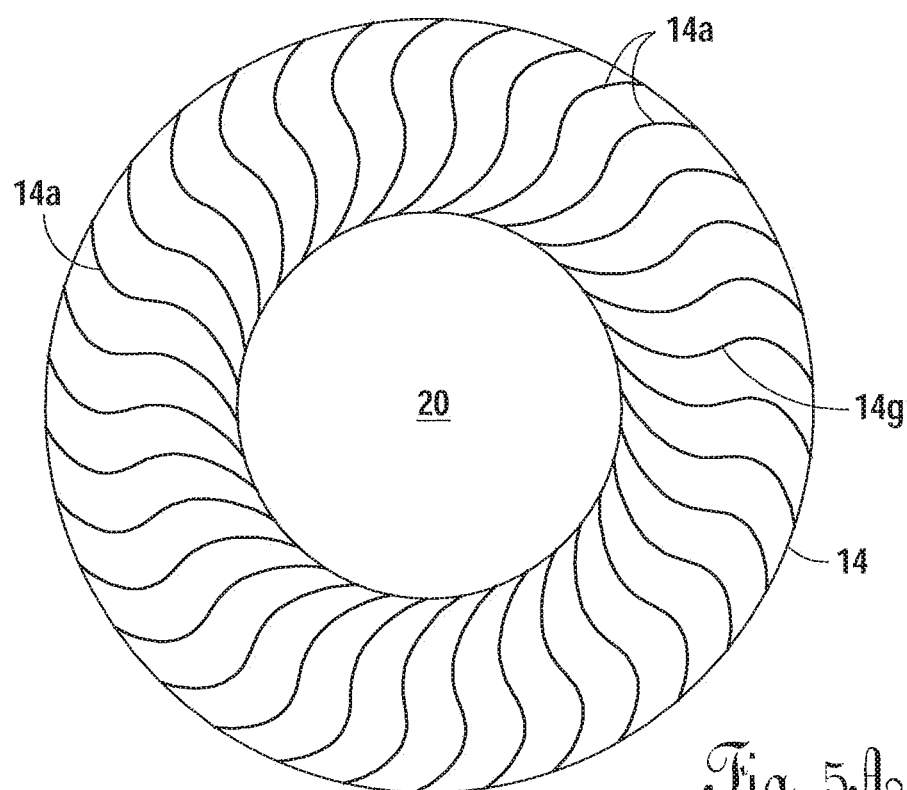
FIG. 5A is a top view of an annular textile supporting sleeve showing a braid variation.
Figure 6A:
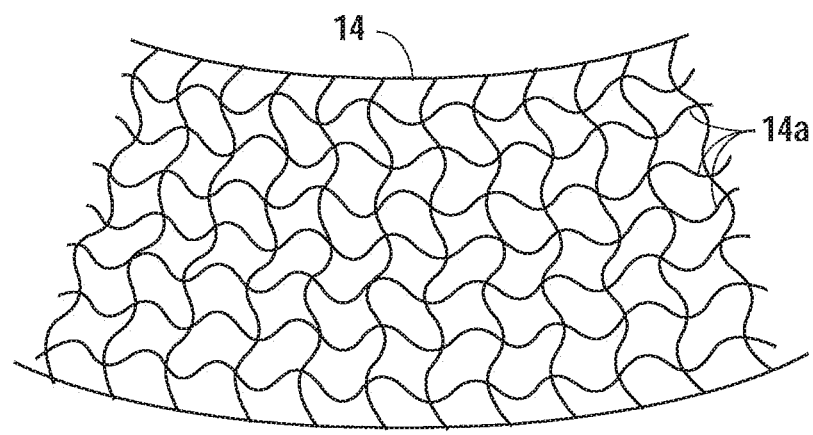
FIG. 6A is an enlarged partial view of an annular textile supporting sleeve illustrating a radial and longitudinal sinusoidal braid variation.
Figure 7A:
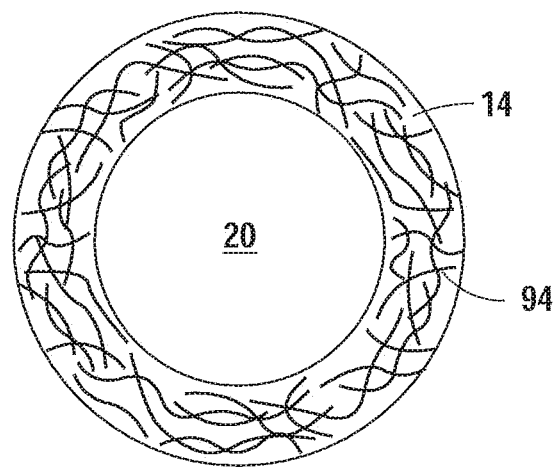
FIG. 7A is a top view of an annular component illustrating annular balloon having a rotational spun fiber coating taken prior to balloon inflation.
Figure 7B:
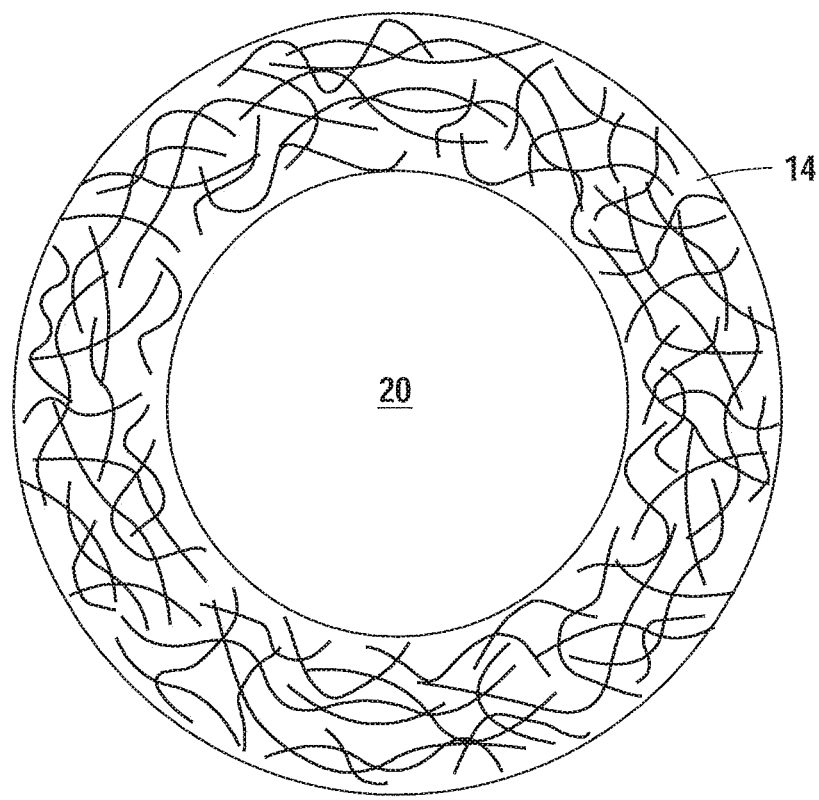
FIG. 7B is a view similar to FIG. 7A taken following balloon inflation and expansion.
Figure 8:
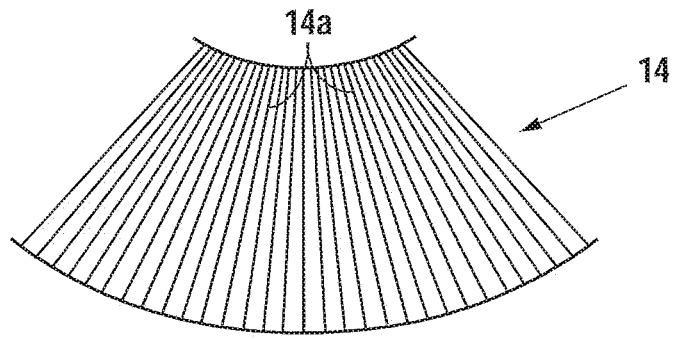
FIG. 8 is an enlarged partial view of an annular balloon provided with corrugations. Note that the corrugations along the lesser curvature of the balloon are more tightly packed than along the greater curvature.
Figure 9A:
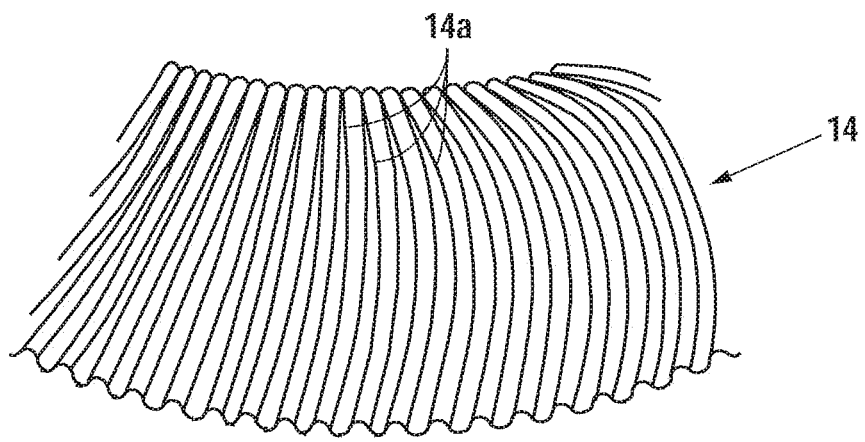
FIG. 9A is an enlarged partial view of an annular textile supporting sleeve demonstrating a curve control arrangement which includes a corrugated textile having controlled expansion restriction along its lesser curvature.
Figure 9B:
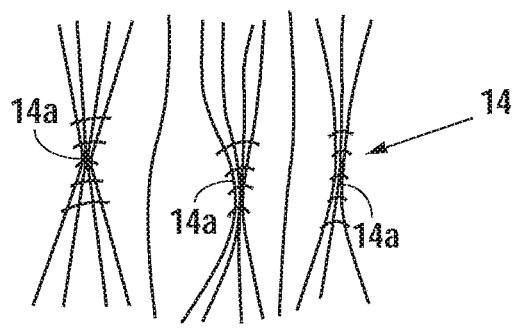
FIG. 9B is a schematic enlarged view of the lesser curvature of the sleeve of FIG. 9A showing a mechanism of expansion restriction done by stitching a number of folds or corrugations which are made in the fabric sleeve.

Referring now to FIGS. 5A, B, FIGS. 6A, B, C, D, FIGS. 7A, B, FIG. 8, and FIGS. 9A, B different embodiments of textile supporting sleeve 14 of the annular component 12 are shown. Generally, the textile supporting sleeve 14 of the present invention is designed to balance the properties of radial and circumferential expansion, kink resistance, and the bunching or jamming effect that occurs when a continuous braid is disposed over an outer circumference of an annular component and then continued over the lesser curvature having a reduced circumference. At the inner curvature of the annular component 12, the fiber density increases as the same number of fibers are made to cover a decreasing circumferential area. One solution may be to utilize sparse braiding to provide greater spacing between fibers. Another solution may be to utilize a braiding pattern that transitions from a single layer to multiple layers as the fabric transitions to the lesser curvature portion of the annular component 12. When the single layer fabric transitions to a multiple layer fabric, the fiber density of a single layer is reduced in each of the multiple layers as each fiber of the single layer is directed to one of the multiple layers.

The circumferential stretch of the annular component 12 of the present invention may about 20-60% of the unstressed circumferential length. Overall the parameters are chosen to provide optimal flexibility and kink resistance to the textile supporting sleeve. In one embodiment shown in FIGS. 5A and 5B the textile supporting sleeve 14 comprises a braided fabric that may be formed as a free standing article that is subsequently pulled over the annular balloon. In one variation, the sleeve 14 is formed from semi-compliant, ribbon-shaped fibers each having a width greater than thickness. In one aspect, the sleeve 14 consists of a flexible annular 3-dimensionally braided structure of polymeric monofilaments and polymeric multifilament yarns 14a.

In reference to FIGS. 5A, B, the multifilament and monofilament yarns 14a are arranged in helices extending around a common central access extending circumferentially around the perimeter of the annular structure. The flexibility of the sleeve 14 is important to allow the device 10 to be packed in a delivery catheter 90, and delivered with minimal friction in deflated form into an intervertebral disc space D. Accordingly, the sleeve 14 has an open mesh construction. A variety of usable thermoplastics are available including polyesters, polyethylenes, polytetrafluoroethylenes, and polyurethanes. The thermoplastic yarns 14a may have a denier from about 30-400, and these may be in the form of multifilament, monofilaments, or spun type. The yarns 14a can be in the form of any conventional configuration, such as flat, twisted, textured, or pre-shrunk. The monofilament and multifilament yarns 14a are inter-braided into axially spaced apart helices that are concentric on a common central axis of the graft.

Longitudinal Flexibility: The longitudinal stretch of the textile supporting sleeve is related to the degree of redundancy provided including the number and size of the folds and creases present in the contracted condition. This redundancy should be kept to a minimum and should remain within the range of variance between the estimated and the actual circumference of the disc space created following discectomy, for example, for a 2×3 cm disc diameter and a circumference of around 6-9 cm, a redundancy of 1 cm may be sufficient. Further longitudinal stretch of the graft is required to provide adequate compliance to the expanded annular implant, and this may be from about 5-20% of the unstressed length of the graft, and preferably 10-15%.

Radial Flexibility: The flexible prosthetic device can accommodate a narrow range of lumen diameters. For example, if a disc height of 8 mm is desired, an 8 mm diameter graft may be designed to expand to 9-10 mm. The favorable combination of strength and flexibility is due to the properties of the strands utilized, and the arrangement of the strands, i.e. the axial spacing and the braiding angles between the adjacent helical strands. The use of a multilayer structure and the optional use of metal wires permits construction of a graft which is both strong and flexible.

Kink Resistance: A desirable property of the present prosthesis is kink resistance. Kink resistance can be defined as a ratio of the bending radius of the longitudinal axis of the graft to the cross-sectional radius. Typically, the kink resistance is between 10:1 ratio and 5:1 ratio. As mentioned previously, improved compliance and kink resistance of the present graft results from providing a space between the outer surface of the elastomeric layer and the inner surface of the braid to avoid compliance mismatch.

Crush resistance: Crush resistance of the present graft is not considered a requirement in view of the presence of the restoring force provided by the pressurized fluid in the lumen. This is unlike the situation in self-expandable or balloon expandable stents where these are used for enlarging and holding a passageway open. In applications such as grafts or stent-grafts used in vascular and biliary applications, it is desirable that the stent-graft be capable of resisting collapse. These are typically balloon expandable or self-expandable to support the luminal wall. When stretched, the graft of the present invention is flat and smooth, with minimal residual peaks and valleys.

Porosity: Preferably the exterior surface of the graft should include pores which are large enough to allow for the entry of connective tissue from the annulus fibrosus into the outer periphery of the graft. Unlike vascular grafts, whereby the inner surface of the graft must have pores small enough so that blood passing through the graft will not leak, the present graft for the annular implant has a separate inner elastomeric layer that is impermeable to fluids.

Manufacturing: The 3-dimensional braided textile supporting sleeve may be formed on a shaped article or mandrel. For example, a braid having a diameter of 10 mm may be formed with tapered ends measuring 5 mm to closely match the dimensions of the valve base to which it is bonded. Additionally, the 3-dimensional braided graft may be formed or shaped on a mandrel or preformed to correspond to the curvature of the inner margin of the annulus fibrosus of particular disc.

Figure 4B:
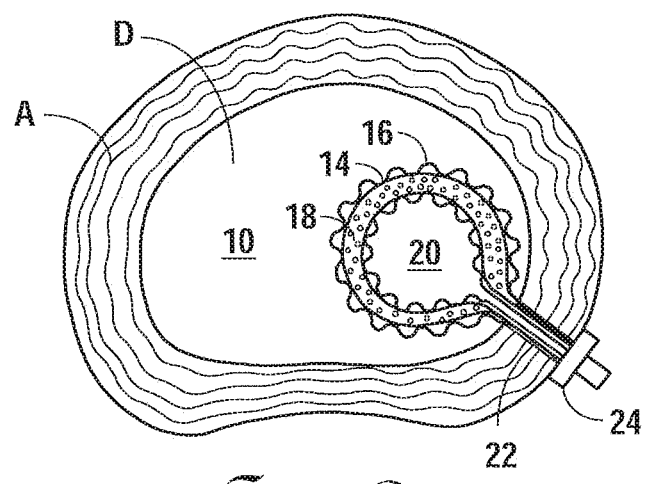
Figure 4C:
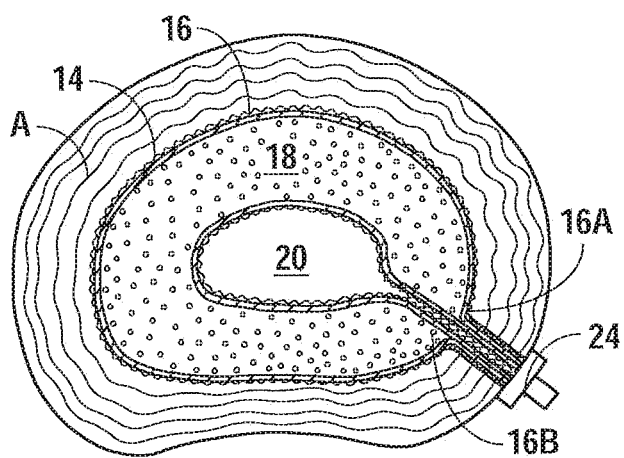

The textile supporting sleeve 14 of the present invention is illustrated in its contracted condition within the disc space in FIG. 4A. In this condition, the annular balloon 16 is in a relaxed contracted condition. Since the textile braid is longer and wider than the contracted elastomeric membrane, it forms fold and creases, with a potential space P formed between the two layers. As illustrated in FIGS. 4B, C, expansion of the inner balloon results from increase in pressure and volume of injected fluid in its inner space 18. This is accompanied by annular elongation and expansion of the textile braid resulting in unfolding of the folds and creases FIG. 4C. In the expanded and elongated condition FIG. 4C, the non-elastic textile braid 14a constrains any further elongation or expansion of the textile supporting sleeve 14 even under high pressure, and protects the balloon 16 from inadvertent over expansion or rupture. The surface of the braid 14a is taut, smooth, and relatively flat when fully stretched. It is also porous, and this has the advantage of allowing ingrowth of fibrocytes and eventual integration with the annulus fibrosus A. The inflated diameter and the circumferential length of the annular balloon 16 can be tailored to the desired dimensions of the disc space in a particular clinical setting.

Figure 5B:
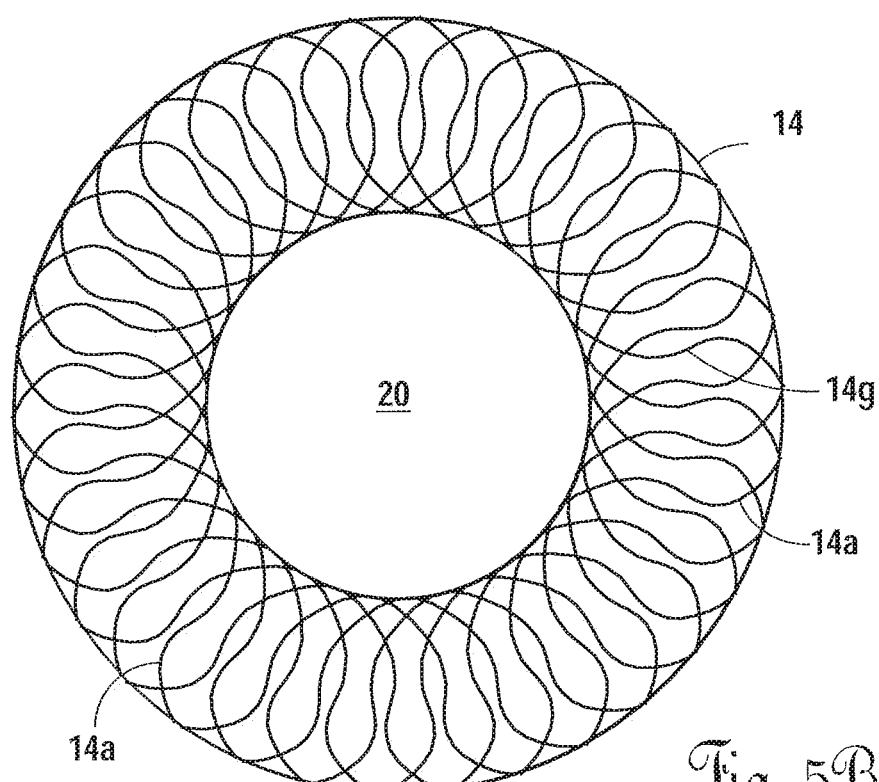
FIG. 5B is a top view of another annular textile supporting sleeve showing an alternative braid variation.

Referring now to FIGS. 5A and 5B, there is illustrated sectional views of envisioned textile supporting sleeve 14 fiber braid reinforcement 14a of annular component 12. The braided textile supporting sleeve 14 may include first and second fiber layers with fibers intertwined in such a way that no two fibers are twisted exclusively around one another. As shown in FIG. 6A, the longitudinal and circumferential fibers (not shown) define a generally sinusoidal pattern. The fibers are substantially semi-elastic and have an elongation to break of around 15%. The fibers may have a thickness of from about 0.0005 to about 0.025 in. and width to thickness ratio in the range of 30:1 to about 40:1. In yet another embodiment, the first and second fiber layers may be woven, knitted, or braided as necessary to provide the necessary balance of strength, flexibility, and endurance.

Figure 6B:
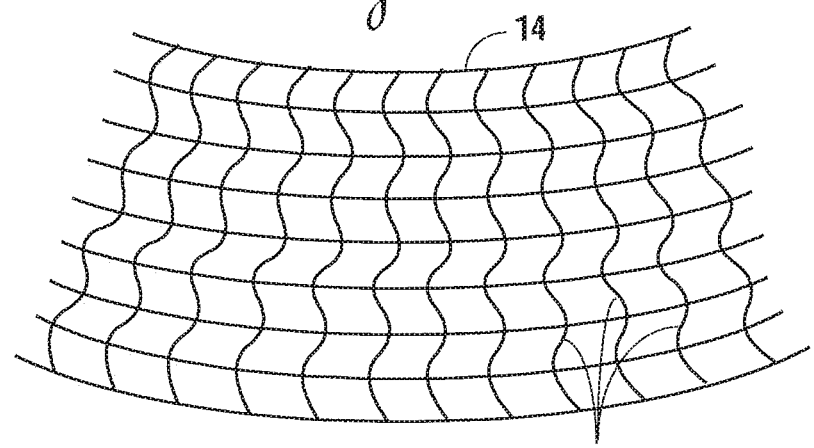
FIG. 6B is an enlarged partial view similar to FIG. 6A illustrating straightening of the longitudinal sinusoidal fibers following stretching of the sleeve in the longitudinal or circumferential direction.
Figure 6C:
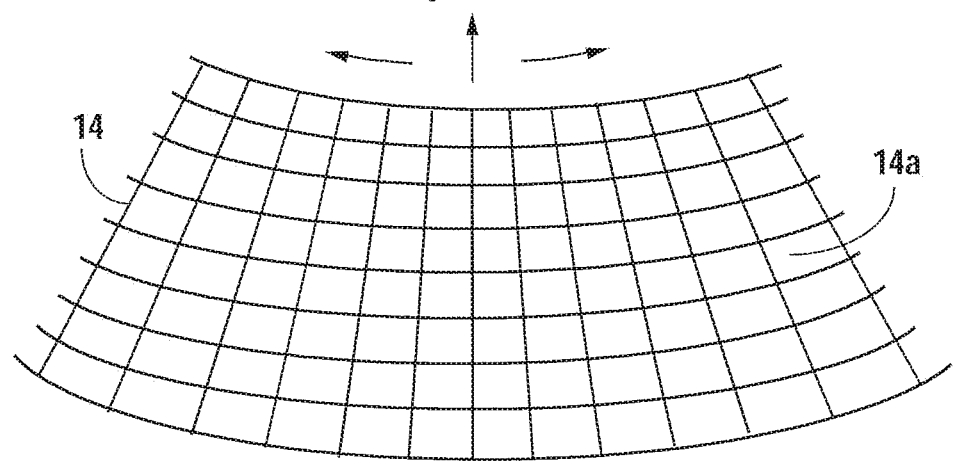
FIG. 6C is an enlarged partial view similar to FIGS. 6A and 6B illustrating straightening of radial and longitudinal fibers following stretching of the sleeve in the longitudinal and radial directions.

Referring to FIG. 6B, the textile supporting sleeve 14 has been stretched along the circumferential direction of the annular component. The longitudinal sinusoidal fibers, have been straightened, restraining further expansion of the annular component 12 in this direction. FIG. 6C illustrates the behavior of the longitudinal and radial fibers when the annular balloon is inflated freely within a disc space, unconstrained by the inner margin of the annulus fibrosus. The forces exerted by annular balloon 16 on textile supporting sleeve 14 cause stretching of the fibers in both directions, straightening the sinusoidal fibers, and constraining further expansion of the annular component 12.

In situations whereby the annular component 12 is slightly oversized with respect to the circumferential perimeter of the intervertebral disc space, the longitudinal sinusoidal fibers would not reach their stretching limit and would provide a shock absorbing function thus contributing to the desired level of dynamic mobility to the vertebral segment. Likewise, in situations when the device 10 is deployed in a relatively narrow disc space, the radial sinusoidal fibers would not be fully stretched when the annular balloon 16 is pressurized. As such, the sinusoidal configuration of the radial fibers provide the latitude to controllably increase device pressurization to widen the disc space and/or differentially expand to correct coronal or sagittal deformity as will be illustrated hereinafter.

Figure 6D:
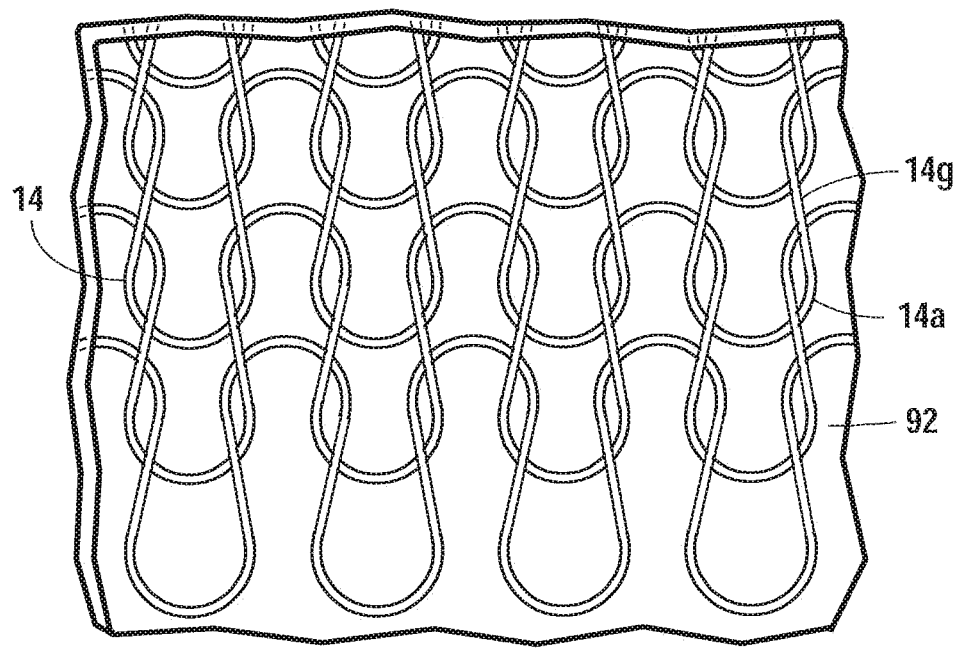
FIG. 6D is an enlarged partial view of an annular textile supporting sleeve having a knitted fiber pattern in accordance with one embodiment of the disclosure.

FIG. 6D illustrates an embodiment of a textile supporting sleeve 14 formed of a semi-elastic knitted pattern 92. Knitted pattern 92 is produced by mechanically intertwining and interlocking fibers in a series of interconnected loops that permit longitudinal and radial expansion and yet preserve appropriate degree of flexibility. The pattern 92 is a warp knitted design having set yarns 14a diagonally shifted of one or more yarns 14a to form a loop between engaging yarns 14a. Various knitted patterns 92 of a textile supporting sleeve 14 are configured to provide flexibility and preserve physiologic mobility similar to the function of an intact annulus fibrosus A, while restraining hyper mobility and/or segmental stability.

Referring to FIGS. 7A and B, there is illustrated an alternative embodiment to the supporting textile sleeve 14 to the annular component 12. In this particular embodiment, one or more layers of rotationally spun fiber coating 94 is provided to the annular balloon. Thus, a multilayered design may be created in which the annular balloon 16 and the fiber matrix 94 are integrated to provide relatively less flexibility than independent and/or separate balloons and textile designs, but more flexibility than single layer design. The preferred embodiment in this particular application is that the layers within the wall of a multilayered annular balloon 16 may be separated such that they are allowed to slide with respect to each other. Such constructs have the added advantage of being thinner, have increased burst strength and are relatively easy to fold or otherwise become packed into a smaller delivery configuration.

Referring to FIG. 8, a corrugated semi compliant annular balloon 16 is provided in which the corrugation along the lesser curvature of the balloon 16 are more tightly packed than along the greater curvature. This arrangement may be feasible through a heat-set process during manufacturing. The advantage of this design is increased filling and packing flexibility, as well as avoidance of kinking or buckling of the annular balloon 16 during deployment.

Referring to FIG. 9A, an even further embodiment of the present invention, a curve control arrangement and/or kinking resistance design is provided which includes a corrugated textile supporting sleeve possessing a controlled degree of differential compliance and expansion restriction. The method of producing such a fabric includes providing an elongate tubular graft of a suitable fabric of polymeric material; providing a mandrel compressing individual ribs or rings corresponding to a specific location such as the inner curvature aspect of an annular textile supporting sleeve; placing the sleeve over the crimp-forming mandrel; applying pressure and/or heat to heat set the pattern.

As demonstrated in FIGS. 9A and B, expansion restriction may be done by stitching or sectional crimping of a number of folds or corrugations which are made in the fabric sleeve, whereby, upon inflation of the annular balloon 16, the diametrically opposed outer circumferential margins of the textile supporting sleeve 14 can extend more than the inner margin, thereby forming a curve in a tubular textile sleeve to form an annular textile supporting sleeve 14.

Figure 10B:
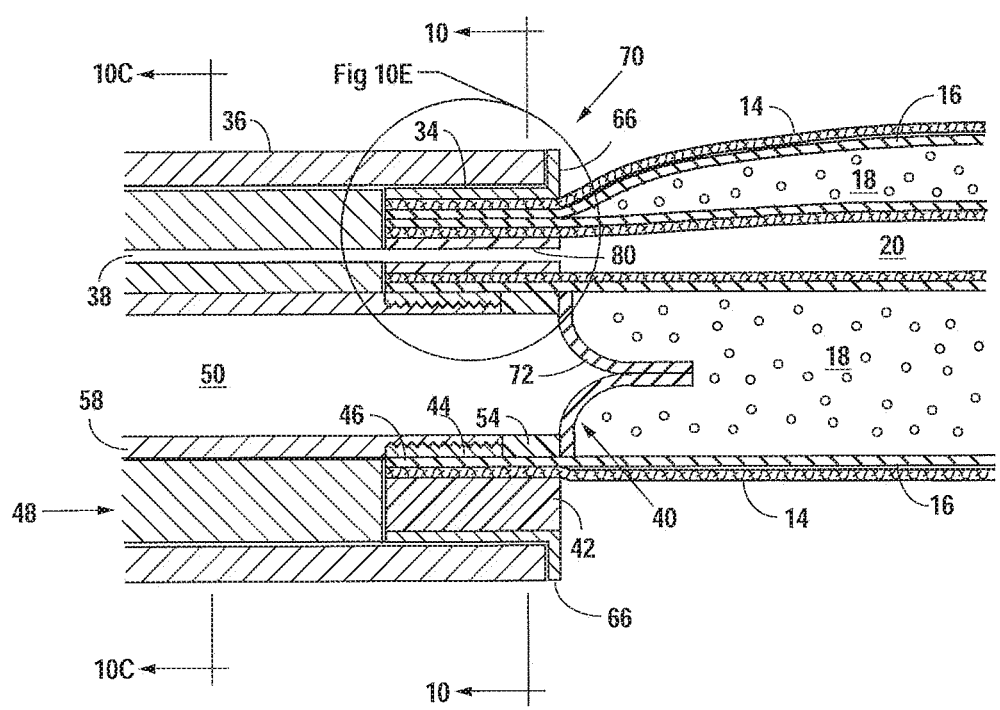
FIG. 10B is a cross-sectional view of the securement element shown in FIG. 10A taken in the axial plane along the line 10B-10B.
Figure 10B:
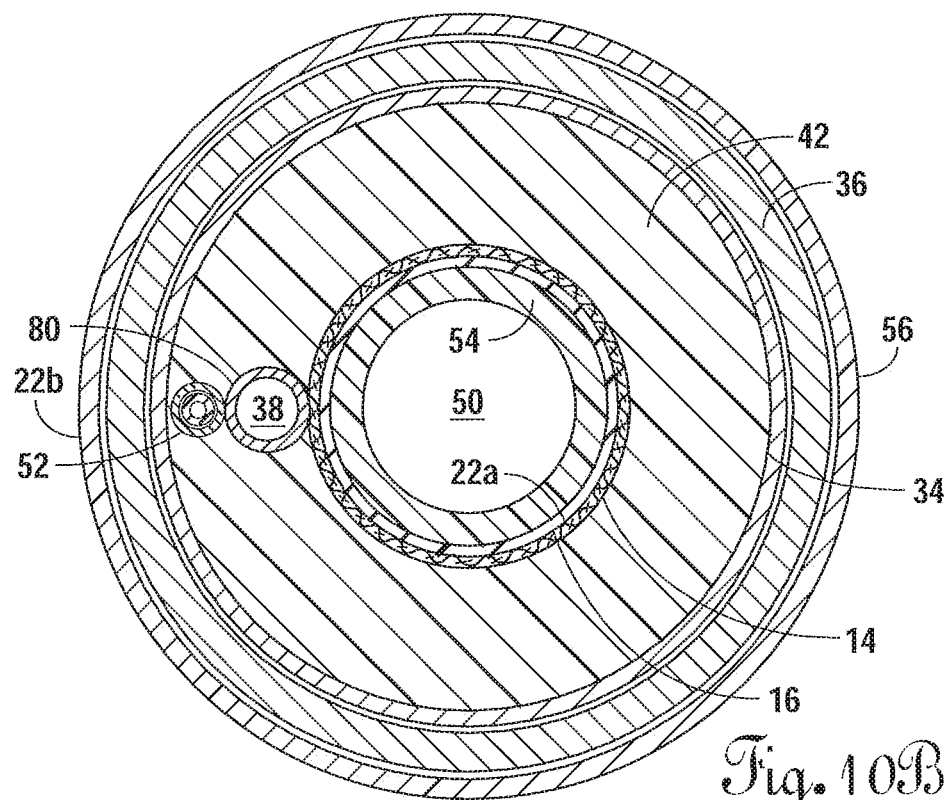

Securement Element: Referring now to FIGS. 10A-F, securement element 24 will now be described in more detail. FIG. 10A shows a cross-sectional view of securement element 24 sealingly affixed to the neck portions 22a and 22b of annular component 12, comprising annular balloon 16 and overlying annular textile supporting sleeve 14. One neck portion 22a is centrally located and is securely bonded to fluid coupling assembly 44 and sealing valve assembly 40 which are interposed between inflation passageway 50 proximally and annular lumen 18 distally. A second neck portion 22b includes a closed distal portion of annular lumen 18, whereby the distal portions of annular balloon 16 and annular textile supporting sleeve 14 are bonded together to obliterate the annular lumen 18, and to secure the distal neck portion 22b to the securement element 24.

Figure 10C:
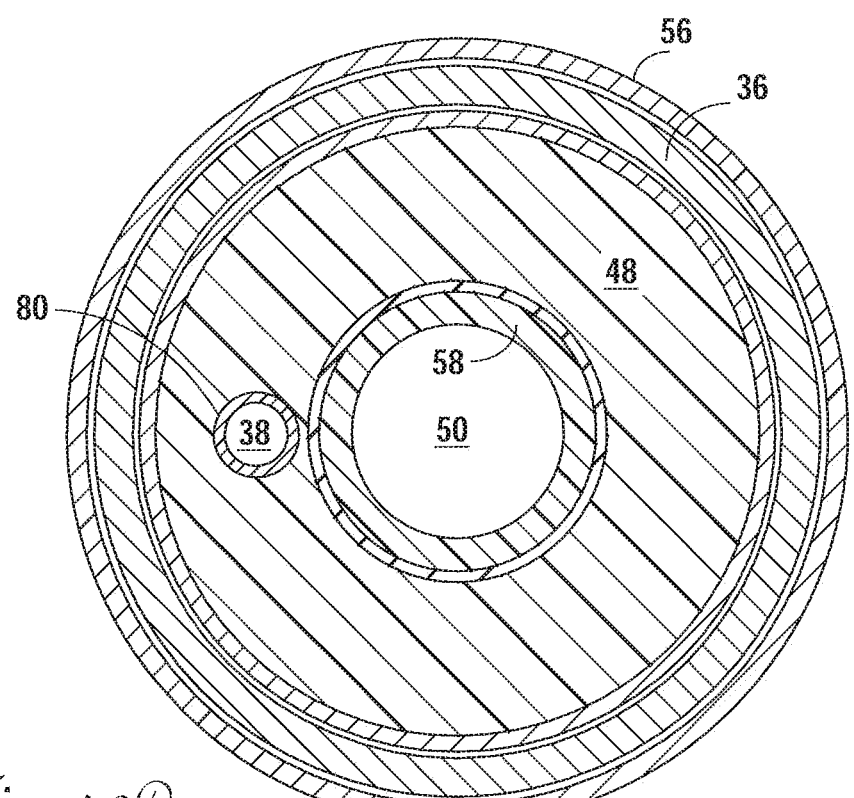
FIG. 10C is cross-sectional view of the securement element shown in FIG. 10A taken in the axial plane along the line 10C-10C.
Figure 10D:
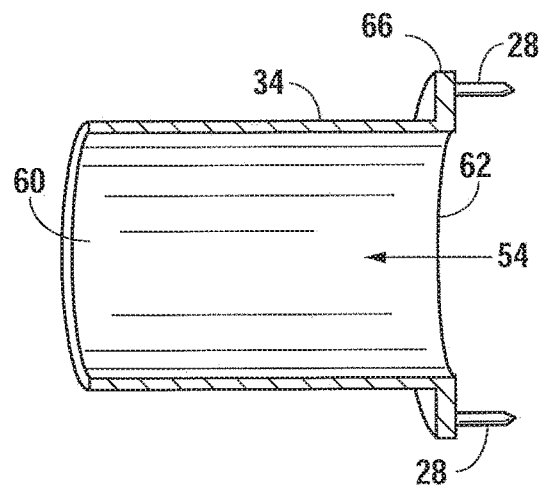
FIG. 10D is a fragmentary cross-sectional view of the cylindrical collar component of the securement element shown in FIG. 10A.
Figure 10E:
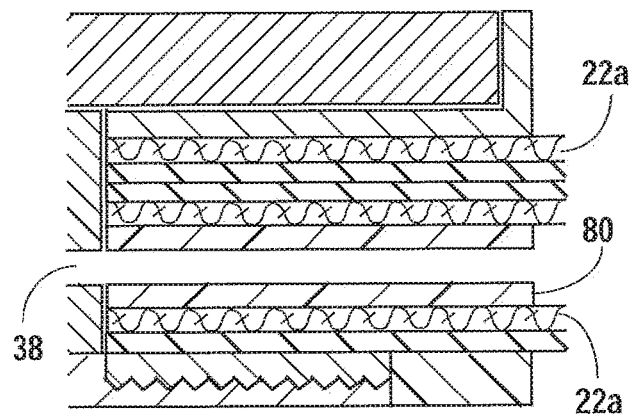
FIG. 10E is an enlarged fragmentary cross-sectional view of the bonded section of the second neck portion of the annular component within the securement element shown in FIG. 10A. Included is shown the high pressure balloon sleeve and passageway there through leading to the interior space of the annular component.

With reference to FIGS. 10A and 10E, there is also shown a high pressure balloon sleeve 80, with a high pressure balloon passageway 38 therein, interposed between the bonded second neck portion 22a and the inflation first neck portion 22b. The high pressure balloon passageway 38 provides access to a removable high pressure balloon 88 to the interior space 20 of the annular component 12 as will be explained hereinafter. Referring to FIGS. 10A, B, and C, the components of the proximal neck portion 22a, distal neck portion 22b, and high pressure balloon sleeve 80 are compactly encased within the passageway of a rigid cylindrical collar 34. A polymeric insert 42 occupies the remaining space within the cylindrical collar 34 passageway.

Turning now to FIGS. 10B, C, and D the cylindrical collar 34 is shown forming the outer portion of securement element 24 having a passageway 54 extending there through, a proximal aperture 60, and a distal aperture 62, and a distal outward flange 66. The flange 66 forms a ring around the distal portion of the cylindrical collar 34. At least two penetrating pins 28 project distally from the distal face of the flange 66 which together, form an attachment element that secures the securement element 24 to the outer margin of the annulus fibrosus A.

Referring to FIG. 10A, there is shown a removable inflation cannula 58 coupled to the fluid coupling assembly 44. Inflation cannula 58 includes external threads 68 at a distal end thereof in mating engagement with internal threads 70 of a fluid coupling ring 46 of securement element 24. The fluid coupling ring 46 is preferably formed of a metal or a rigid polymer and provides strong mechanical support to the adjacent valve base 54 and proximal portion of annular balloon 16 and textile supporting sleeve 14.

More distally, within the longitudinal passageway 64, a sealing valve assembly is included. The sealing valve assembly 40 comprises an annular valve base 54 adjacent the distal portion of fluid coupling ring 46, having an identical outer diameter. Valve base 54 is cylindrical, having a passageway there through and an inner wall which is smoothly continuous with an inner wall of inflation cannula 58 of fluid coupling assembly 44. The valve base 54 is formed from a firm rubber to provide support and structural integrity to sealing valve assembly 40 mounted the distal portion of valve base 54.

In one embodiment, a self-sealing miter or duck bill valve 72 is provided for the sealing valve assembly 40. The duck bill valve 72 is formed of one or two sheets of a silicone elastomer sheeting, or other flexible material having a suitable thickness as for example 0.005-0.010 of an inch. The sheets have a generally rectangular configuration, and their edges are fastened to the distal face of the valve base 54 by a suitable adhesive, preferably a silicon adhesive.

FIG. 10B is a cross-sectional view taken in the axial plane along the line 10B-10B of securement element 24 shown in FIG. 10A. As shown, the polymeric insert 42 occupies a relatively large portion of the cylindrical collar 34 passageway. The cylindrical collar 34 has a thin wall of metal or strong rigid polymer such as PEEK. The polymeric insert 42 is preferably formed of a firm rubber. The inflation passageway 50 is centrally located, surrounded concentrically by the valve base 54, annular balloon 16, and the textile supporting sleeve 14. These three layers are bonded by adhesive RF or other ways known in the art.

As shown in FIGS. 10A, B, the bonded distal portion of the annular component 12 is located in the periphery of the securement element 24, surrounded by polymeric insert 42. Between the centrally located inflation neck portions 22a and the peripherally located bonded neck components 22b is the high pressure balloon sleeve 80. Balloon sleeve 80 is preferably formed of a metal or firm polymer having a frictionless smooth inner surface configured to provide minimal resistance to insertion and removal of the deflated high pressure balloon 88 and catheter 86.

With further reference to FIGS. 10A and B, there is noted a removable pusher implement 36, slidable between the inner margin of the delivery cannula 56 and the outer margin of the cylindrical collar 34. Pusher implement 36 may be formed of metal or firm polymeric material and has a distal face that rests on the proximal face of the flange 66 of the cylindrical collar 34. When driven forward or tapped on by a mallet, pusher implement 36 cooperates with the flange 66 to drive penetrating pins 28 of attaching apparatus 26 into the outer margin of annulus fibrosus A to anchor the securement element 24 thereon.

Figure 10F:
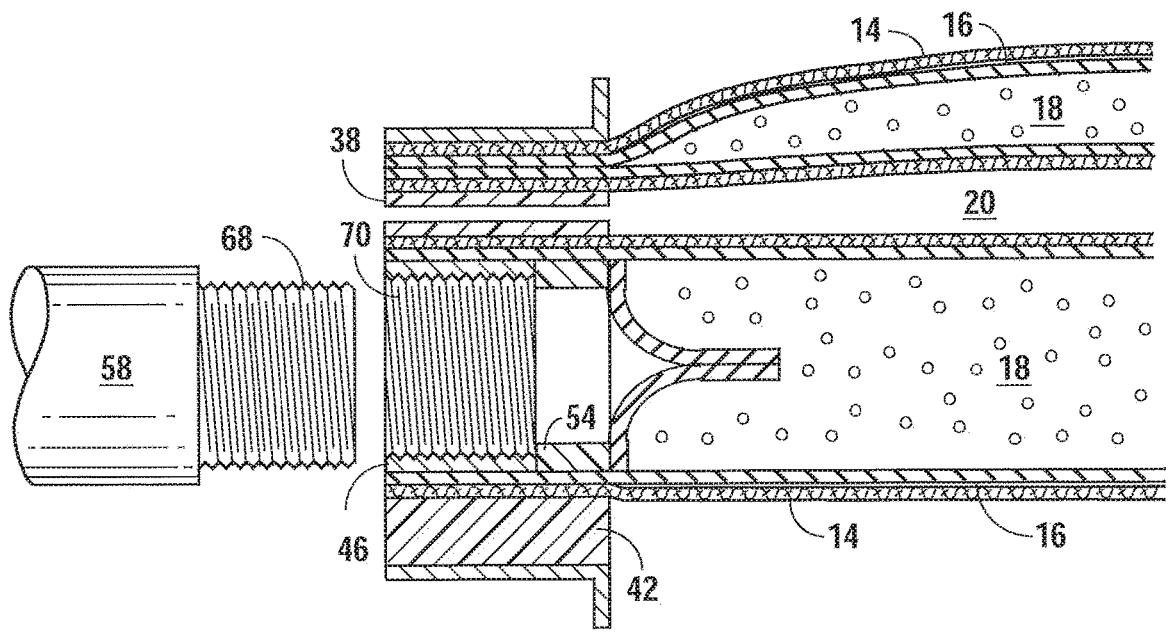
FIG. 10F is a fragmentary cross-sectional view of the securement element similar to FIG. 10A showing the fluid coupling ring and the internal threads thereof following removal of the threaded portion of the inflation cannula.

FIG. 10C is a cross-sectional view in the axial plane taken along the line 10C-10C of FIG. 10A. At this level, a disengagement implement 48 is seen interposed between the inner margin of the pusher implement 36 and the outer margin of inflation cannula 58. High pressure balloon sleeve passageway 38 extends longitudinally within disengagement implement 48 to deliver the high pressure balloon 88 to corresponding high pressure balloon sleeve 80 within the securement element 24, to the interior space 20 of the annular component 12. Disengagement implement 48 also serves the purpose of stabilizing the securement element 24 during the decoupling step of inflation cannula 58 from the securement element 24 while unscrewing the external threads 68 from the fluid coupling ring 46 as demonstrated in FIG. 10F. FIG. 10F is a cross-sectional view similar to FIG. 10A showing the appearance of securement element 24 following removal of inflation cannula 58 from the fluid coupling ring 46.

Figure 11:
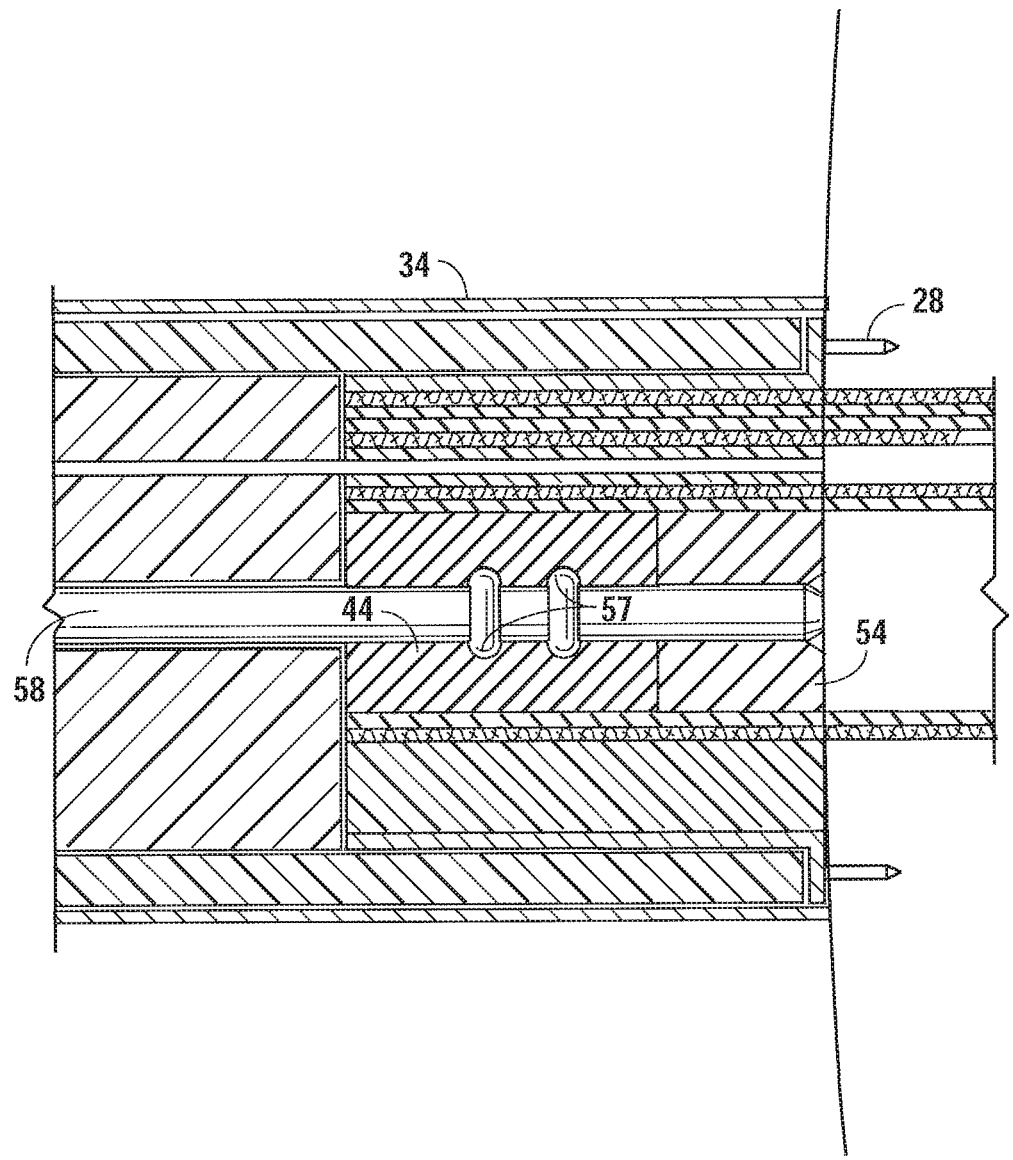
FIG. 11 is a fragmentary cross-sectional view of a securement element demonstrating an alternative embodiment of the fluid coupling assembly and self-sealing valve assembly when compared with FIG. 10A. An inflation cannula has been advanced through the passageways with its tip positioned at the entrance of the annular lumen.
Figure 12:
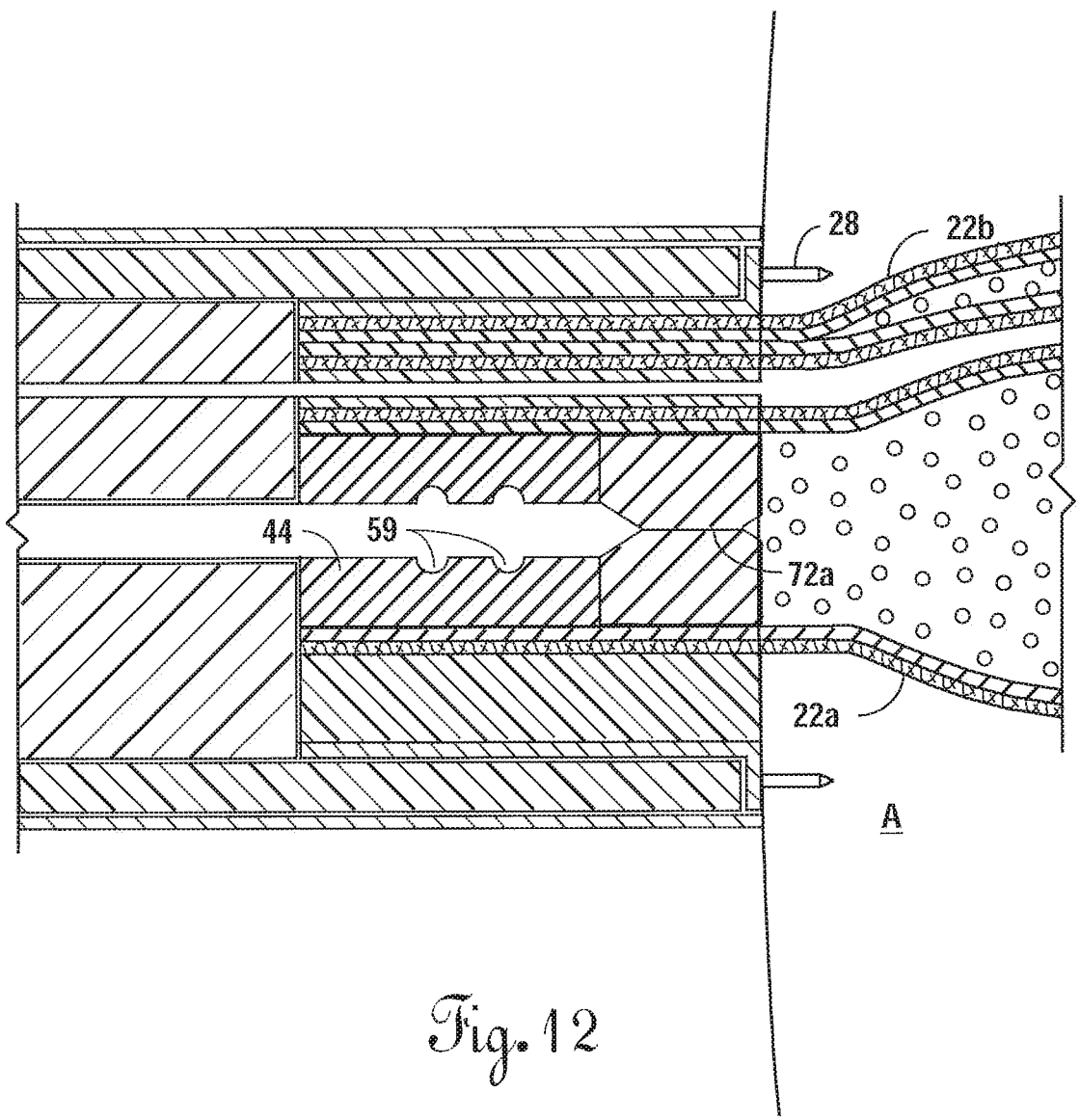
FIG. 12 is a fragmentary cross-sectional view of the securement element similar to FIG. 11 taken following removal of the inflation cannula and closure of the inflation slit in the self-sealing valve.

Referring to FIG. 11 and FIG. 12, an alternative embodiment of the fluid coupling assembly 44 and the sealing valve assembly 40 is provided. In this particular embodiment, the fluid coupling assembly 44 and the sealing valve assembly 40 are different from the assemblies shown in FIGS. 10A-F. FIG. 12 demonstrates a inflation cannula 58 releasably secured to the fluid coupling assembly 44 by a pair of ridges 57 formed on the outer periphery of inflation cannula 58 and mating pair of grooves 59 formed around the periphery of the fluid coupling assembly 44. The engagement of the ridges 57 with the walls of the grooves 59 holds the inflation cannula 58 firmly within the inflation passage 50 to prevent inadvertent fluid leakage or inflation cannula 58 dislodgment during high pressure inflation of the prosthetic device 10. The self-sealing valve 72a may be formed form a firm resilient rubber having a central slit that can dilate to accommodate the inflation cannula 58 in fluid tight engagement. When the inflation cannula 58 is withdrawn, the rubber recoils forming valve slit 72a and thus preventing fluid back flow.

In a preferred technique for removing the inflation cannula 58 from its engagement with the inflation passageway 5, a negative pressure is applied by the operator on the cannula 58 to insure that valve closure has occurred. Forward pressure is then applied on the disengagement implement 48, relative to the inflation cannula 58 causing the ridges 57 to separate from the grooves 59 and causes the distal aspect of the cannula 58 to be withdrawn from engagement with the self-sealing valve 72a. At this point, the inflation cannula 58, disengagement implement 48, delivery cannula 56 and access cannula 84 may be safely withdrawn.

Figure 13:
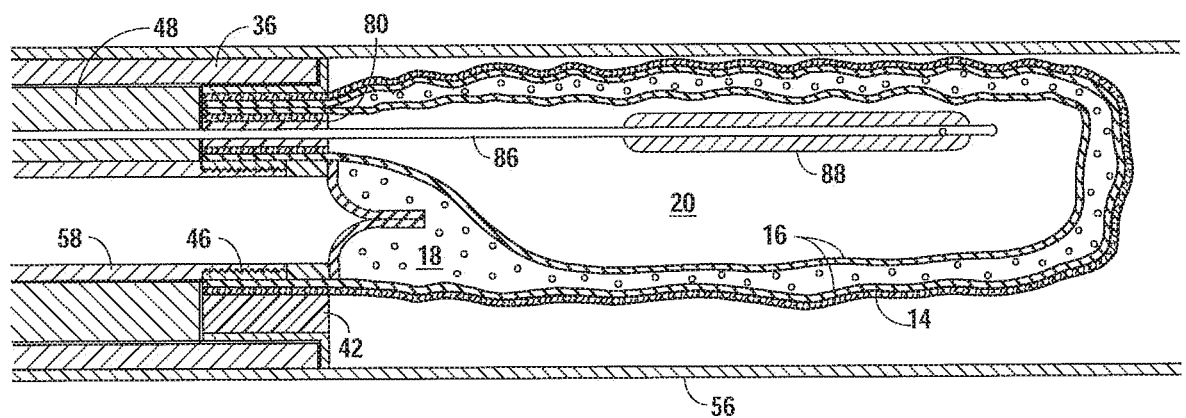
FIG. 13 is a schematic assembled cross-sectional view of the loading portion of the delivery cannula, with the compacted prosthetic device including the high pressure balloon therein.
Figure 14:
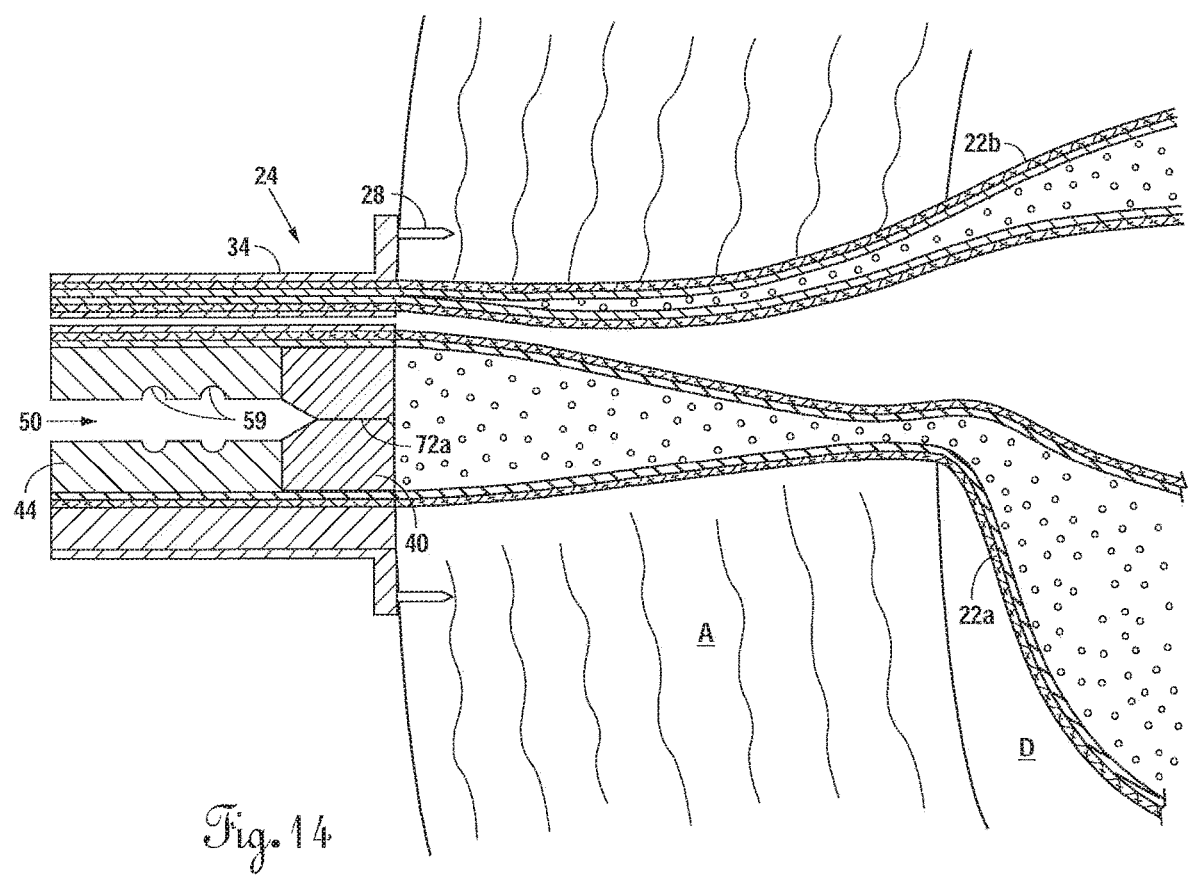
FIG. 14 is an enlarged top cross-sectional view illustrating placement of a securement element along the outer margin of an annulus fibrosus, with first and second neck portions of the annular component extending within the annulus aperture, following partial inflation of the annular lumen with liquid silicone. Notice the alternative embodiment of the fluid coupling assembly and the sealing valve assembly when compared with FIG. 10A.

Referring now to FIG. 13, there is illustrated the loading portion of delivery cannula 56 housing the prosthetic device 10, including the securement element 24, the removable high pressure balloon 88, inflation cannula 58, disengagement implement 48, and pusher implement 36. For purposes of illustration, the different components illustrated in FIG. 14 are not necessarily to scale. The collapsed annular lumen 18 defines a fluid tight space extending between the valve portion and the bonded distal portion of securement element 24, enclosed by the impermeable annular balloon 16 and overlying textile supporting sleeve 14. The high pressure balloon catheter 86 runs along the longitudinal length of the disengagement implement 48 within a high pressure balloon sleeve 80 that continues within the polymeric insert 42 of securement element 24, and terminates in the interior space 20.

The high pressure balloon 88 is collapsed to a minimal profile within the interior space 20. During deployment, the high pressure balloon catheter 86 is advanced until its tip engages the annular component 12, and stretches it longitudinally towards the disc space D. The securement element 24, including the attached inflation cannula 58, are then all advanced in unison until the securement element 24 is at the level of the outer margin of the annulus fibrosus A as visualized fluoroscopically. Furthermore, a stop mechanism may be configured to keep the securement element 24 in appropriate position with respect to the outer margin of the annulus fibrosus A within the delivery cannula 56.

With reference to FIG. 14, there is shown a securement element 24 anchored at the outer margin of the annulus fibrosus A. The neck portions 22a and 22b of a partially inflated annular component 12 extend from the disc space D through an annulus aperture. The first neck portion 22a provides an inflation lumen and is coupled to the sealing valve assembly 40, and the fluid coupling assembly 44 in the passageway of cylindrical collar 34.

Referring to FIGS. 15A-J, implanting intervertebral elastomeric device 10 can begin with a conventional minimally invasive surgical approach, preferably from a lateral retroperitoneal trans-psoas approach. For example, the procedure may be performed on a patient with symptomatic degenerative lumbar scoliosis with the aim of achieving sagittal and coronal balance, pain relief, motion preservation, and restoration of dynamic balance. Conventional surgical approaches sometimes involve multiple anterior releases, followed by a posterior procedure in which deformed correction and surgical stabilization is completed. However, the extent of the anterior surgical release is not universal, and patients selected for this particular procedure may demonstrate some degree of persistent mobility of the vertebral segments on preoperative stress radiographic or CT examination.

The patient is placed in the lateral decubitus position, preferably with the greater curvature of the scoliosis to the side of the surgeon, and the affected level is localized under fluoroscopic observation. The surgeon uses lateral retroperitoneal blunt dissection to expose the lateral surface of the spine. An arm-mounted expandable retractor is placed and discectomies are performed as needed, while preserving the anterior and posterior longitudinal ligaments. The annulus fibrosus A of the intervertebral disc to be treated is penetrated by the pointed end 74a of a guide pin 74, which extends to the contralateral third of the disc space, as seen on the fluoroscopic image. The guide pin 74a may be tapped with a mallet.

Figure 15A:
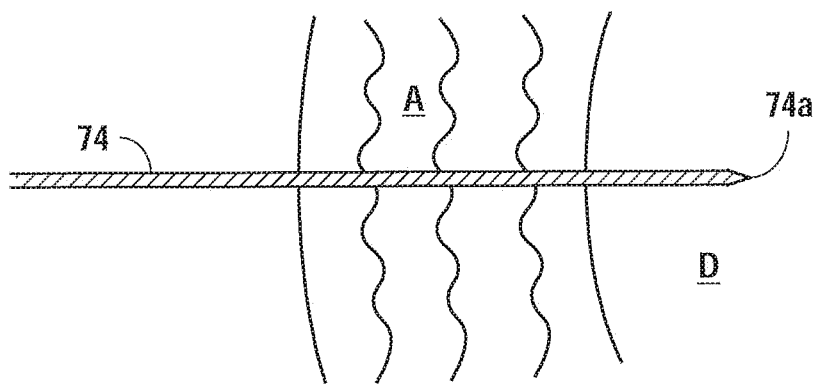
FIGS. 15A, B, C, D, E are sectional views illustrating guide pin insertion through an annulus fibrosus to gain access to a disc space, followed by telescopic insertion of four sequential dilators.
Figure 15B:
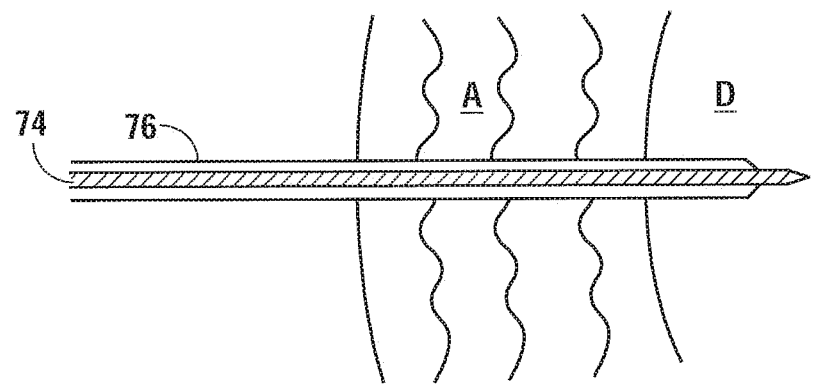
FIG. 15F is a sectional view similar to FIG. 15E illustrating telescopic insertion of an access cannula over the dilators.
FIG. 15G is a sectional view similar to FIG. 15F showing the access cannula extending through the annulus fibrosus with its tip in the disc space. The guide pin and dilators have been removed.
FIGS. 15I, J, K, L and M show sequential steps of device deployment into the disc space and anchoring of the securement element to the outer margin of the annulus fibrosus.
Figure 15C:
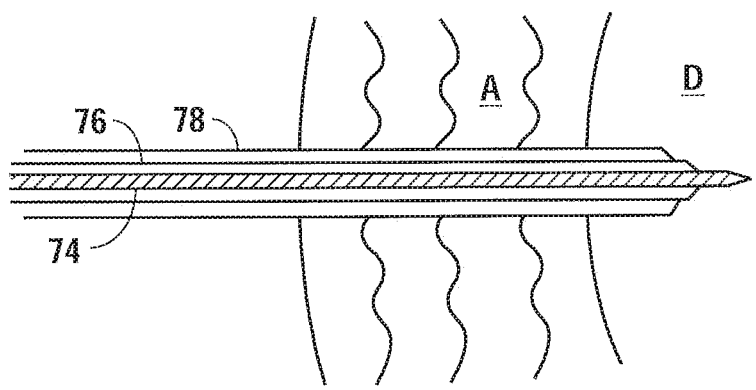
Figure 15D:
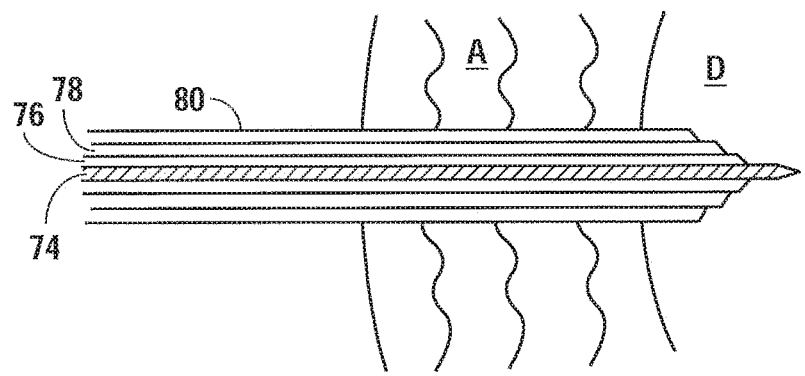
Figure 15E:
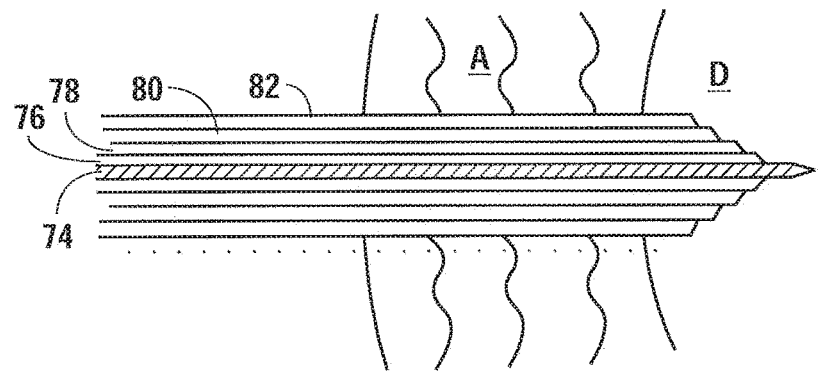
Figure 15F:
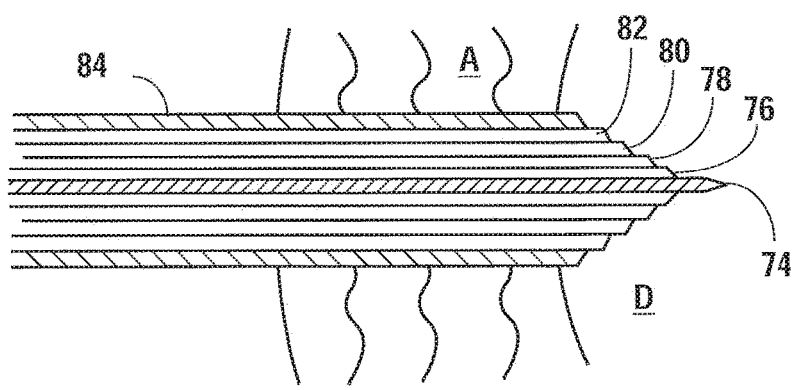
Figure 15G:
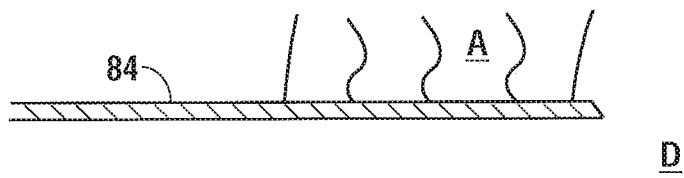
Figure 15H:
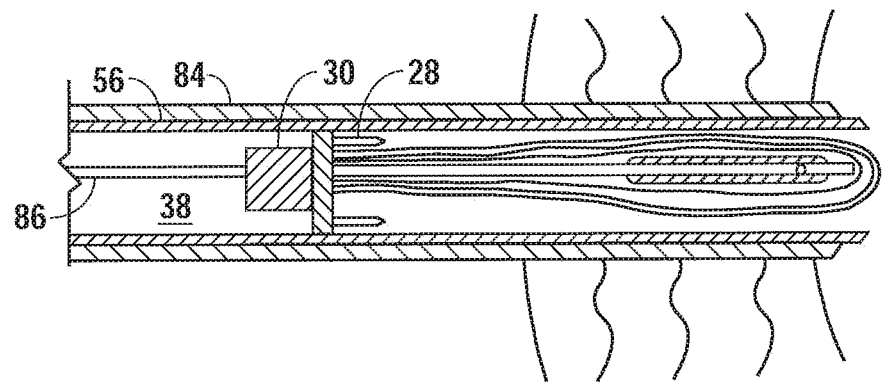

FIG. 15B shows a first rigid dilator 76 inserted over the guide pin 74. FIGS. 15C, D, and E show the telescopic insertion of a second, third, and fourth dilators, 78, 80 and 82, respectively. The dilators 78, 80 and 82 are tubular members of appropriate wall thickness chosen to facilitate overlying insertion of an access cannula 84 as shown in FIG. 15F. FIG. 15F shows telescopic insertion of an access cannula 84 over the successive dilators 78, 80 and 82 to the level of the inner margin of the annulus fibrosus A. With the guide pin 74 dilators 76, 78, 80 and 82 and access cannula 84 in position, the guide pin 74 and four successive dilators 76, 78, 80 and 82 are withdrawn together as shown in FIG. 15G. Turning now to FIG. 15H, delivery cannula 56, with the radially expandable annular reinforcement device 10 including the annular component 12, securement element 24, and the high pressure balloon 88 therein has been slidably inserted into the lumen of the access cannula 84.

FIG. 15H shows that the access cannula 84 has been partially withdrawn to the level of the outer margin of the annulus fibrosus A. The high pressure balloon 88 together with the annular component 12 have been advanced into the disc space D. The securement element 24 remains stationed within the delivery cannula 56 outside the level of the annulus fibrosus A and is secured proximally by the attached inflation cannula 58.

Figure 15I:
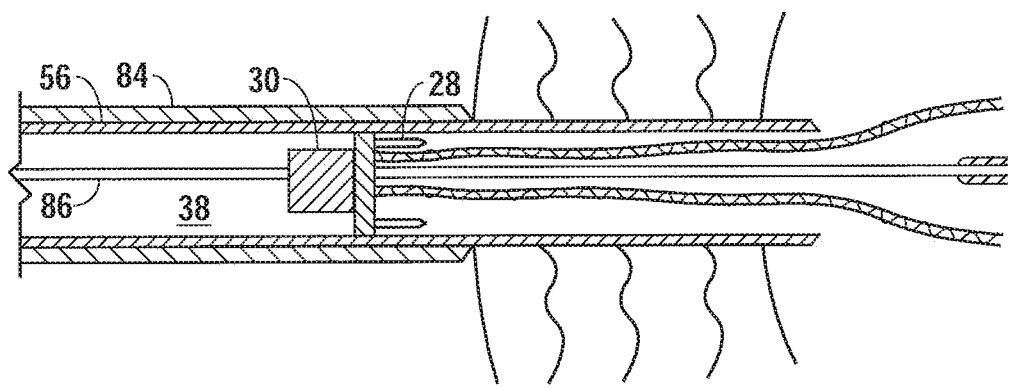
Figure 15J:
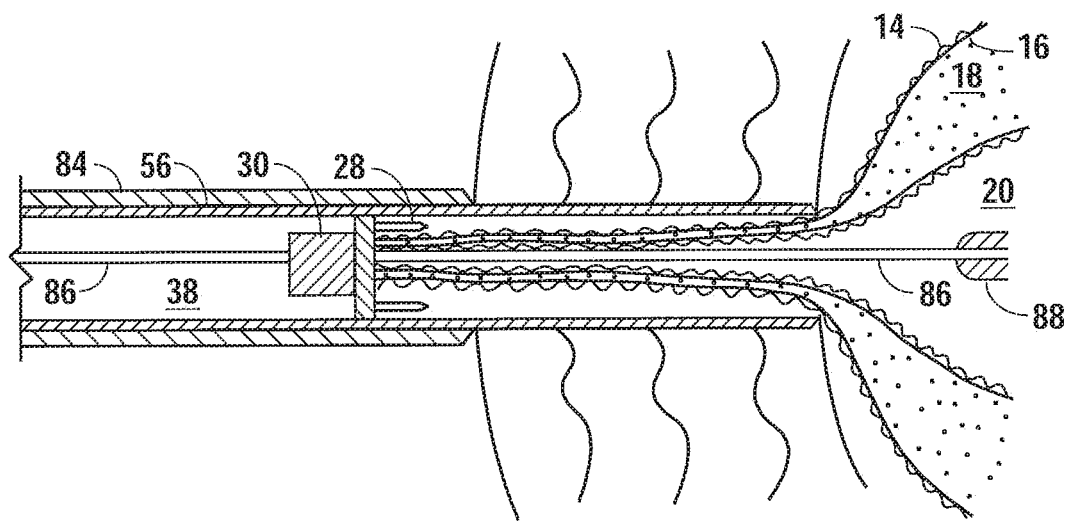

FIG. 15I shows initial inflation of the annular component 12 with in-situ curable medical grade RTV (Room Temperature Vulcanizing) liquid silicone. There is also initial inflation of the high pressure balloon 88 with radiopaque fluid. Optionally, the tip of the delivery cannula 56 may be partially withdrawn into the annulus fibrosus A in order to avoid inadvertent penetration of the annular component 12 following further balloon expansion.

Figure 15K:
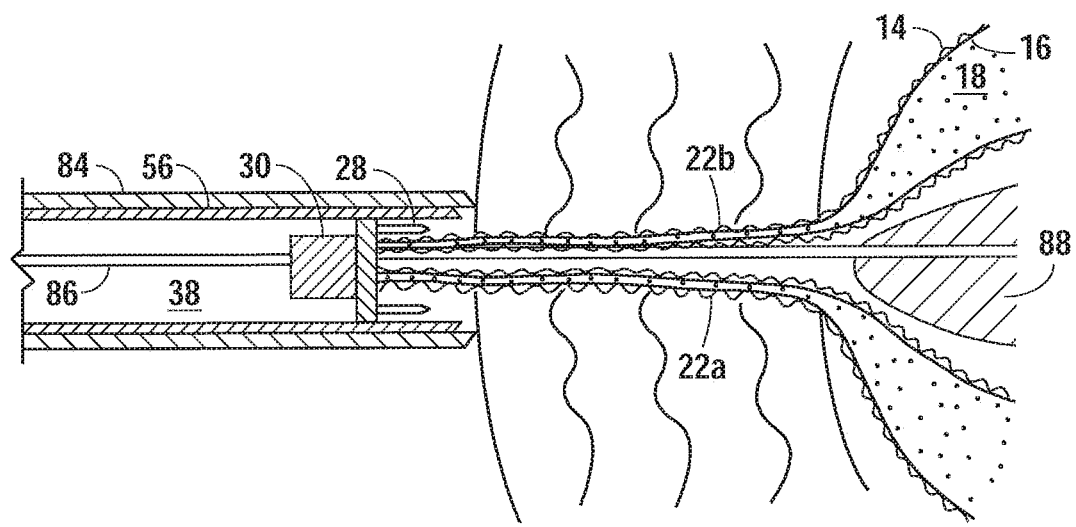

FIG. 15K shows further inflation of the high pressure balloon 88 and the annular component 12. Alternating balloon inflation proceeds at this point under fluoroscopic observation and pressure monitoring to achieve optimal disc space widening, and deformity correction. Preferably, inflation of high pressure balloon 88 and annular component 12 is monitored by independent pressure gauges coupled to both systems. When the operator is satisfied with the achieved result, he/she retracts the delivery cannula 56 and the access cannula 84 to a level outside of the outer margin of the annulus fibrosus as shown in FIG. 15K.

Figure 15L:
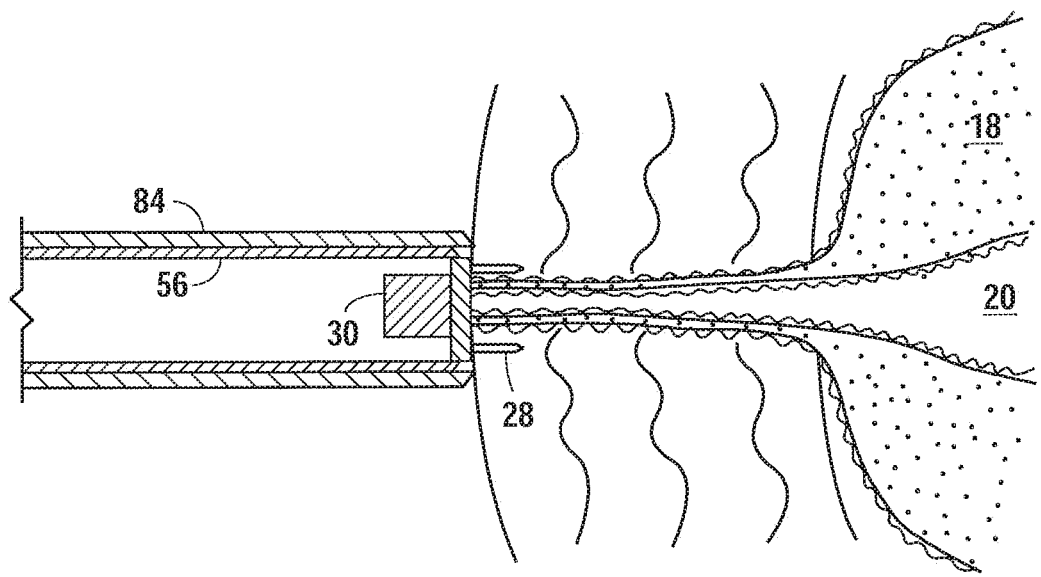
Figure 15M:
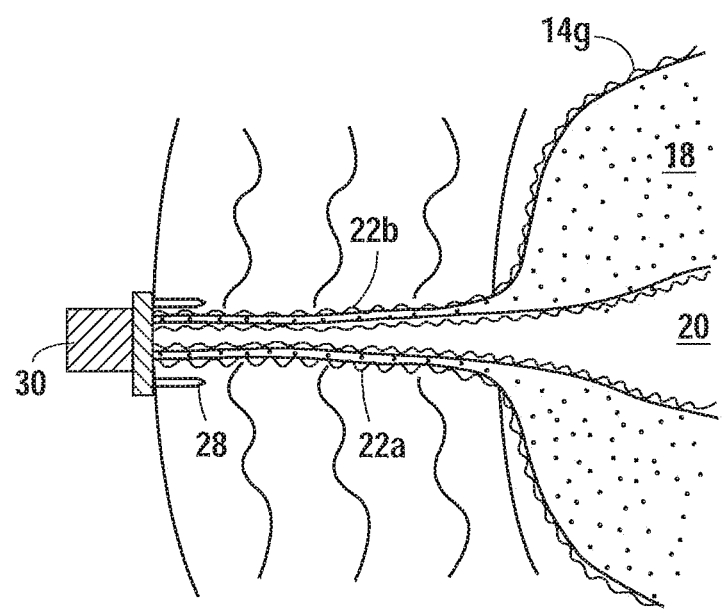

As the delivery cannula 56 and access cannula 84 exit the penetrating passage formed in the annulus fibrosus A, the annulus fibrosus A contracts and squeezes the corresponding portions of the annular component 12 to form the neck portions 22a and 22b. Referring to FIG. 15H, the securement element 24, including the attaching apparatus 26 are driven forward towards the annulus fibrosus A by the pusher implement 36. The penetrating pins 28 penetrate the outer margin of the annulus. FIG. 15L shows that the delivery cannula 56 and access cannula 84 have been withdrawn; the securement element 24 is anchored in position, the annulus fibrosus aperture is contracted around the neck portion 22a and 22b, and the high pressure balloon 88 has been withdrawn, and the annular component 12 is fully inflated with curing or cured silicone.

Figure 16A:
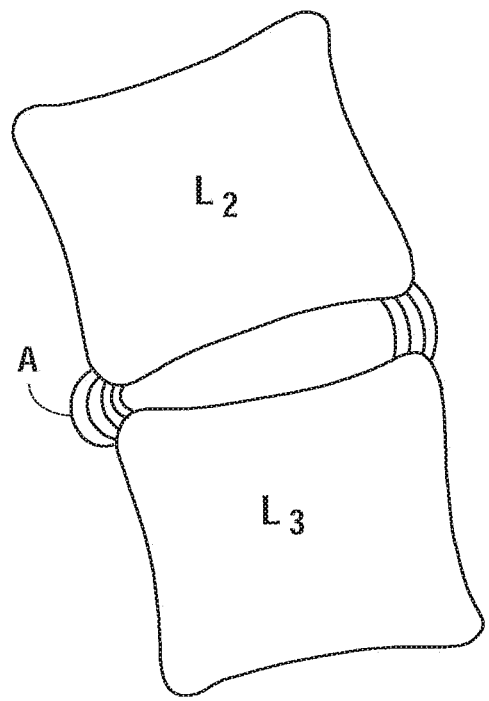
FIG. 16A is a frontal schematic representation of an L2-L3 vertebral segment affected by adult degenerative lumbar scoliosis (ADLS).
Figure 16B:
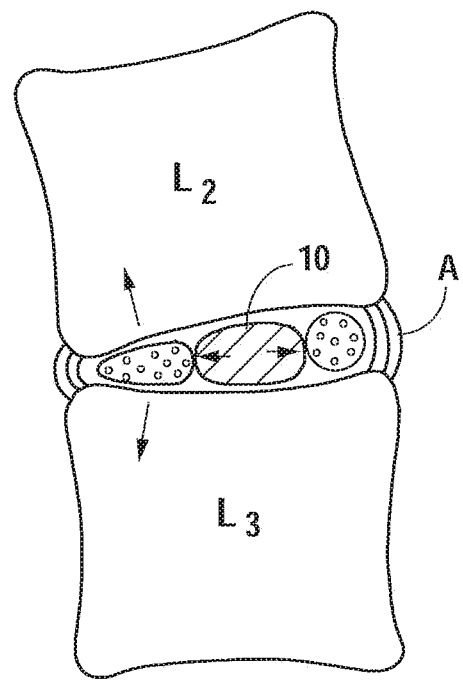
FIG. 16B is a frontal schematic view similar to FIG. 16A following implantation of the prosthetic device within the affected disc space, and initial inflation of the annular component with liquid silicone and inflation of the high pressure balloon with contrast material. At this stage, the high pressure balloon exerts an outward expansion force on the annular component to displace it towards the narrowed portion of the disc space. Notice that the portion of the annular component within the narrowed aspect of the disc space is relatively flat and oval at this stage.

Referring to FIGS. 16A-D, FIG. 16A is a frontal schematic view of the lumbar spine affected by ADLS showing levoscoliosis centered at L2-L3. Unilateral disc height loss is present. FIGS. 16B, C and D demonstrate a high pressure balloon 88 in the central aspect of the disc space and segments of the annular component 12 are seen in cross-section. High pressure balloon 88 is inflated with radiopaque contrast material and can be easily visualized on fluoroscopy during the procedure. The annular component 12 is inflated with liquid elastomer, preferably in-situ curable silicone that has been rendered radiopaque by a medium such as barium.

Referring now to FIG. 16B, early inflation of the high pressure balloon 88 and early inflation of the annular component 12 is associated with circumferential outward displacement of the annular component 12. There is essentially no pressure on the superior and inferior end plates at this point. Upon further alternating inflation of the balloon 16, there is further outward migration of the annular component 12 towards the periphery of the disc space. Since the fluid pressure within the annular component 12 is still rather low, a segment of the annular component 12 is still relatively flat and migrates into the narrowed aspect of the disc space, as shown in FIGS. 16B and 16C.

Figure 16C:
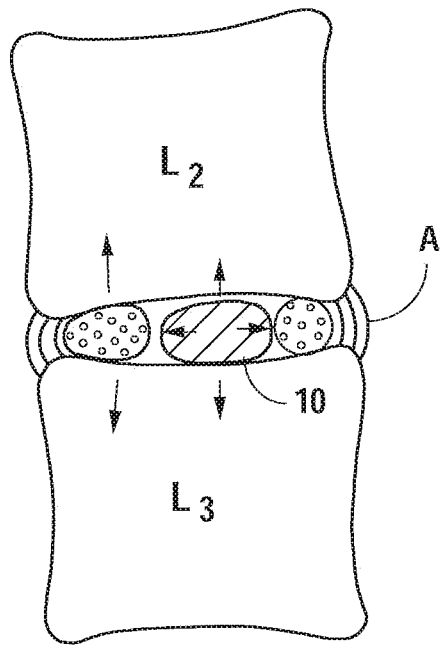
FIG. 16C is a frontal schematic view similar to the view in FIG. 16B following further expansion of the annular component as well as the high pressure balloon. At this stage, the high-pressure balloon is exerting a distraction force on the superior and inferior end plates as well as an outward circumferential force on the annular component to squeeze it further into the narrowed aspect of the disc.

FIG. 16C shows further expansion of the high pressure balloon 88, which at this stage exerts a broad-based force on the superior and inferior end plates. This pressure is preferably applied gradually and under fluoroscopic observation, and pressure monitoring of both balloons to ensure not to exceed a certain pressure limit that might lead to fracturing of the end plate, especially in patients with osteoporosis. Increasing pressure within the annular component 12 exerts pressure along the peripheral aspect of the end plates, which is stronger than the central aspect and may be able to withstand higher pressure. Accordingly, it is desirable to alternate increase in pressure between the high pressure balloon 88 and the annular component 12 until an optimal result is obtained.

Figure 16D:
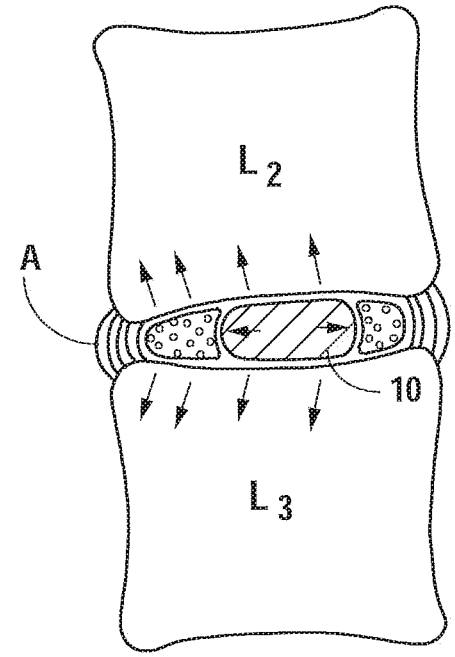
FIG. 16D is a frontal schematic view similar to FIG. 16C showing appreciable correction of the vertebral deformity which was present in FIG. 16A.

With reference to FIG. 16D, the high pressure balloon 88 has assumed an oval configuration with generally flat superior and inferior margins along the end plates. There has been maximal migration of the annular component 12 to the periphery of the disc space, including migration into the narrowed aspect of the disc space which was present in FIG. 16A. There has been appreciable correction of the angular deformity. At this point, the high pressure balloon 88 may be deflated and removed. However, in some instances, it may be advisable to maintain the inflated high pressure balloon 88 until the liquid silicone has cured to insure that the scoliosis reduction is maintained. The timing of silicone cure could be selected by the physician prior to the procedure and may be within a 30-60 minute range if so desired.

Figure 17A:
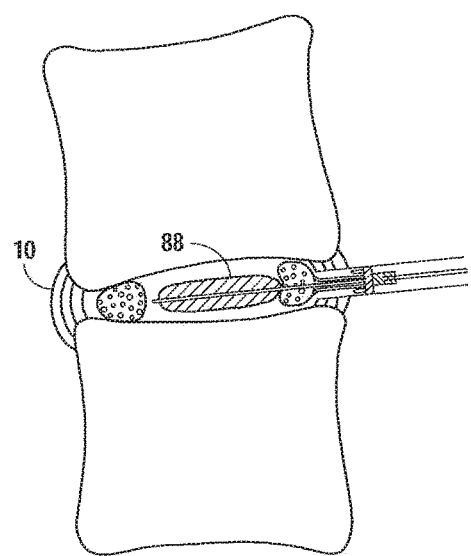
FIG. 17A is a frontal schematic representation of an L4-L5 vertebral segment affected by ADLS.
Figure 17B:
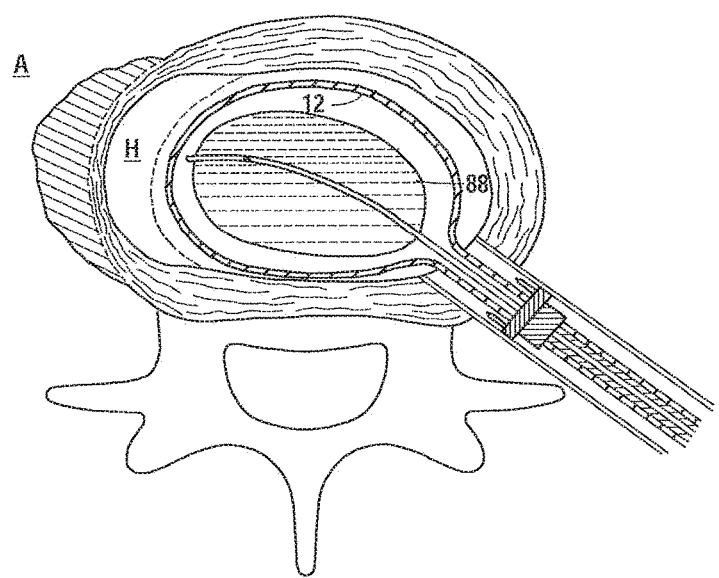
FIG. 17B is an axial schematic view at the L4-L5 disc shown in FIG. 17A demonstrating an extruded annulus fibrosus fragment leaving a defect in the annulus fibrosus. The high pressure balloon and annular component are only partially inflated.
Figure 17C:
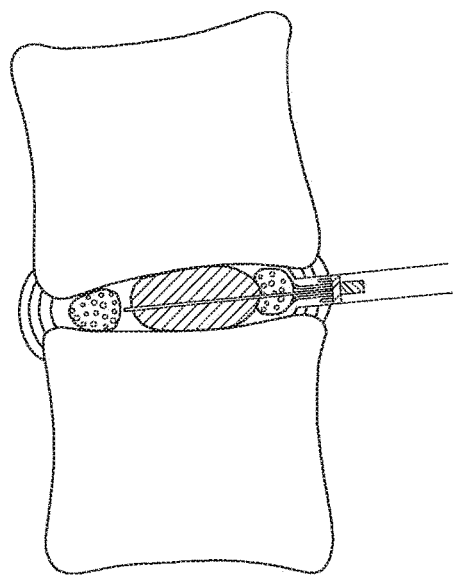
FIG. 17C is a frontal schematic view similar to FIG. 17A showing further inflation and pressurization of the high pressure balloon and the annular component.
Figure 17D:
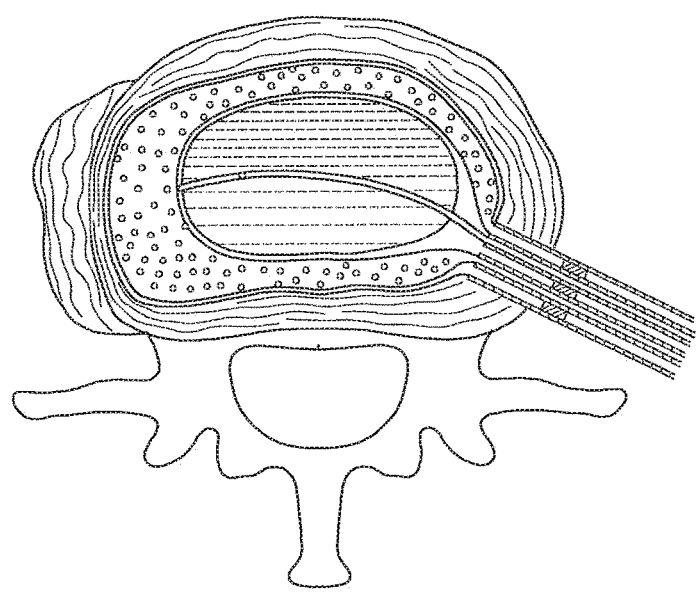
FIG. 17D is an axial schematic view similar to FIG. 17C showing further balloon inflation. The annular component showing relatively increased expansion extending into the defect of the annulus fibrosus and has filled this defect.

FIGS. 17A and B are frontal and axial schematic views demonstrating typical changes seen in degenerative scoliosis. There is asymmetrical disc space narrowing associated with disruption of the annulus fibrosus, and lateral annulus fibrosus migration in this region, instability in the sagittal and coronal planes, and there is often bone on bone opposition of the adjacent vertebrae. The disruption in the annulus fibrosus is demonstrated in FIGS. 17B and H FIGS. 17A, B, C and D demonstrate extension of the annular component 12 of the prosthetic device 10 inflated with liquid silicone into the annulus fibrosus defect, seen best in FIG. 17B.

Figure 17E:
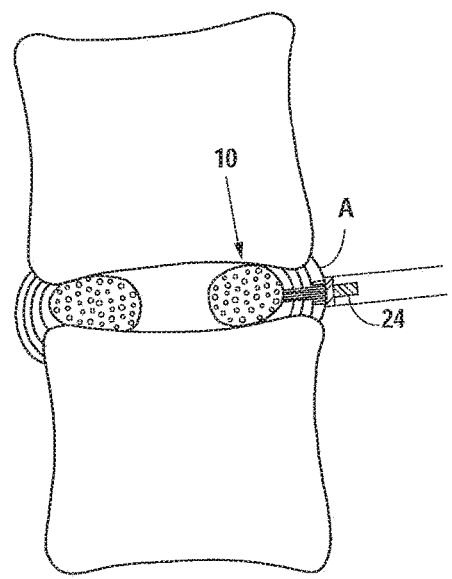
FIG. 17E is a frontal schematic view similar to FIG. 17C, following removal of the high pressure balloon.
Figure 17F:
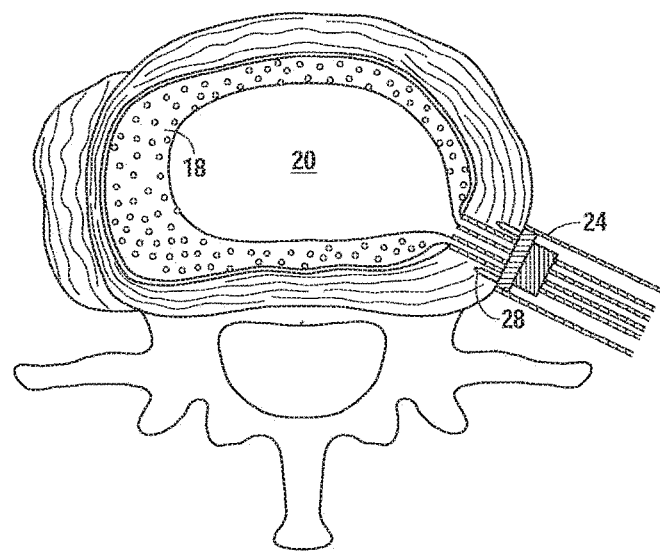
FIG. 17F is an axial schematic view similar to FIG. 17D following removal of the high pressure balloon.

FIGS. 17E and F are similar to FIGS. 17 C and D, except that the high pressure balloon 88 has been removed.

Figures 17G, 17H:
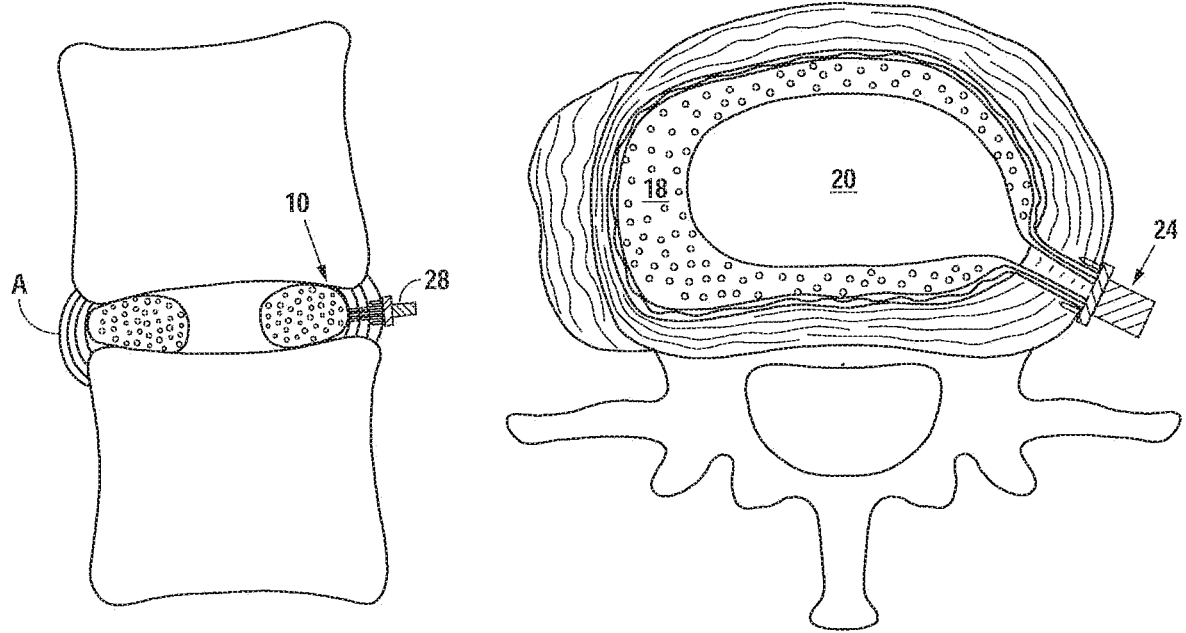
FIG. 17G is a frontal cross-sectional view similar to FIG. 17E taken following removal of the access and delivery cannulas. The securement element is seen in position anchoring the annular component to the annulus fibrosus. The contralateral aspect of the annular component has extended into the annulus defect, providing augmentation. There has also been appreciable correction of the coronal deformity at this level.
FIG. 17H is an axial schematic view similar to FIG. 17F taken following removal of the access and delivery cannulas.

FIGS. 17G and H demonstrate that the delivery and access cannula 84 have been removed and the securement element 24 is seen in position providing secure attachment and attaching to the annular component, in optimal contralateral position to the annular defect.

Figure 18A:
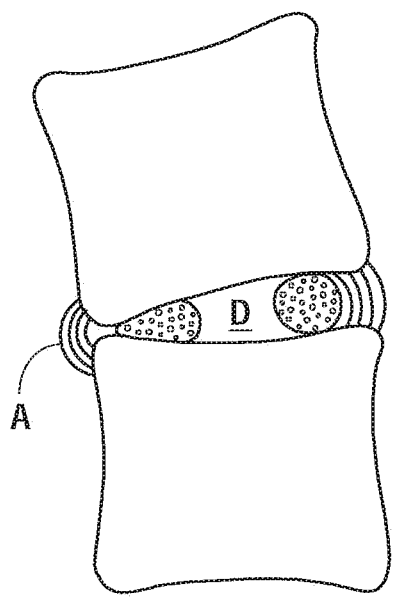
FIG. 18A is a frontal schematic representation of an L3-L4 vertebral segment affected by ADLS. In this case, the annulus fibrosus is completely outside its normal position, and there is bone-to-bone opposition of the adjacent vertebral bodies. The annular component segment in this region is markedly flattened as it extends outwards into the narrowed space previously occupied by the annulus fibrosus.
Figure 18B:
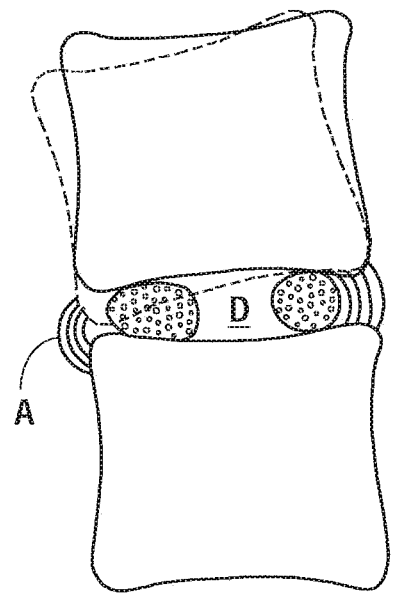
FIG. 18B is a frontal schematic representation of the same level as FIG. 18A demonstrating differential expansion of the annular prosthesis component to fill the annulus fibrosus defect, providing augmentation and deformity correction. The dotted line outlines the position of the L3 vertebral body prior to the procedure.

FIGS. 18A, B, and C demonstrate a case of severe degenerative scoliosis whereby there has been complete lateral disruption of the annulus fibrosus associated with vertebral segment instability at this level. Asymmetrical and/or differential expansion of the annular component 12 is demonstrated, with an expanded segment occupying the relatively large annular defect, while restoring vertebral alignment.

Figure 18C:
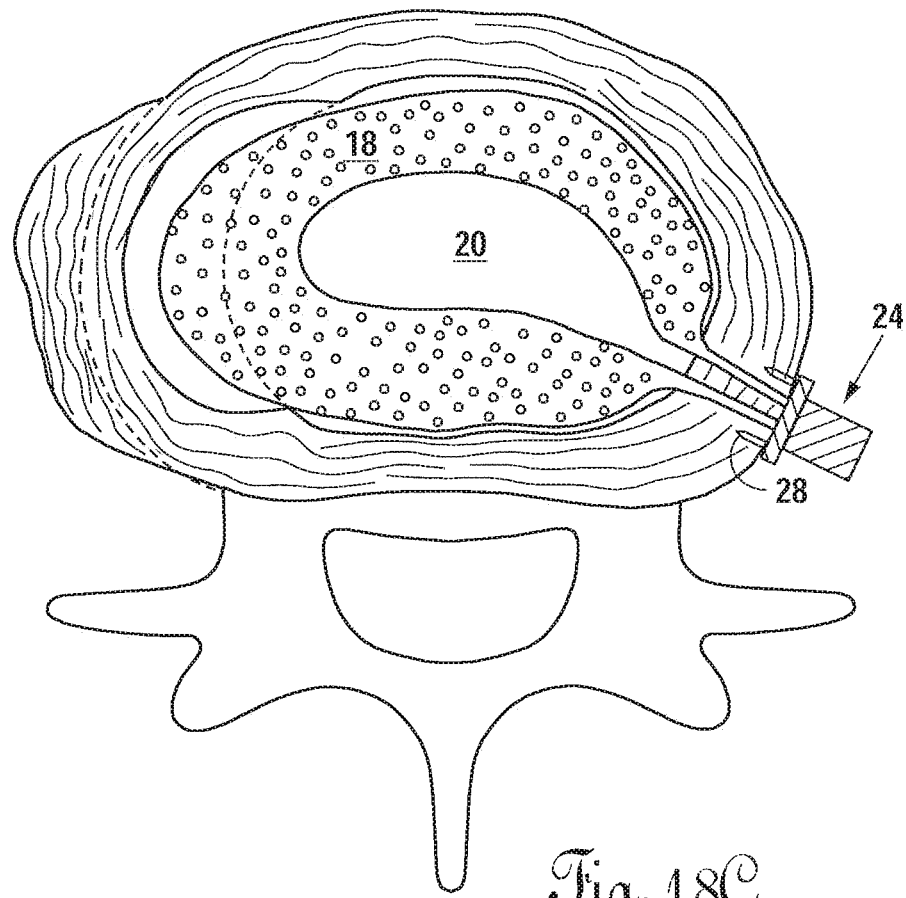
FIG. 18C is an axial schematic representation of FIG. 18B showing prosthesis extension to fill the annulus defect.
Figure 19:
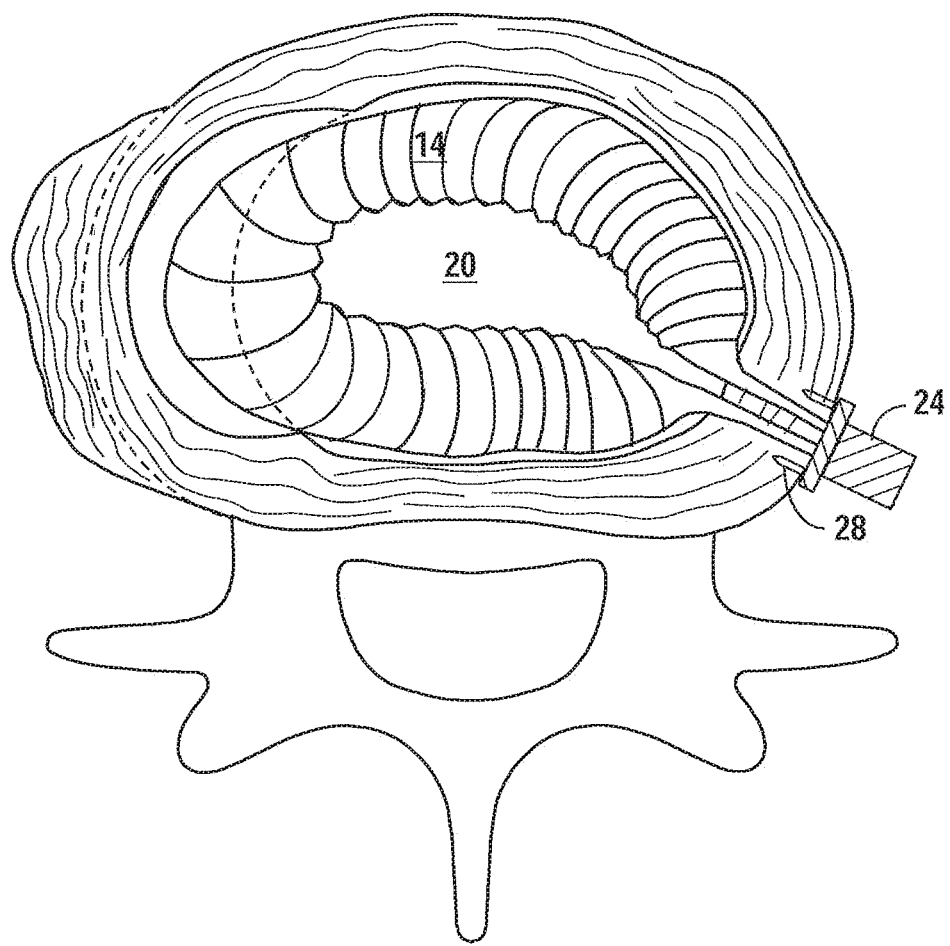
FIG. 19 is a top schematic view similar to FIG. 18C showing an alternative embodiment of an annular component having a corrugated textile supporting sleeve.

FIG. 19 is an axial view similar to FIG. 18C, in which a corrugated textile supporting sleeve is utilized.

Figure 20A:
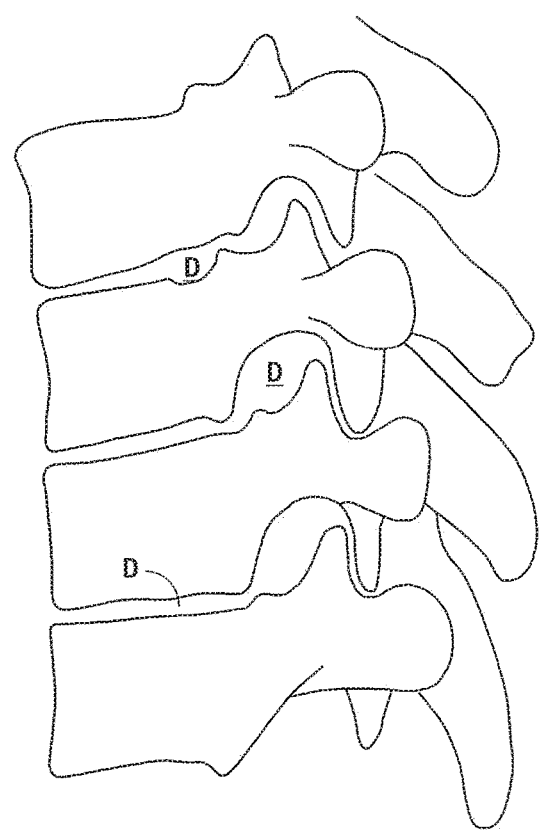
FIG. 20A is a sagittal, perspective view of a lumbar spine showing abnormal, degenerative straightening of the lumbar lordosis.

FIG. 20A is a lateral schematic view of the lumbar spine demonstrating loss of lumbar lordosis with multilevel disc space narrowing and degenerative changes throughout the spine. Normal lumbar lordosis is essential for the lower back to perform in a healthy manner. Elderly people with degenerative lumbar disease are characterized by a flat back with a significant structural and/or postural reduction in lumbar lordosis, which is correlated with an increase in lower back pain and a decrease in function.

Figure 20B:
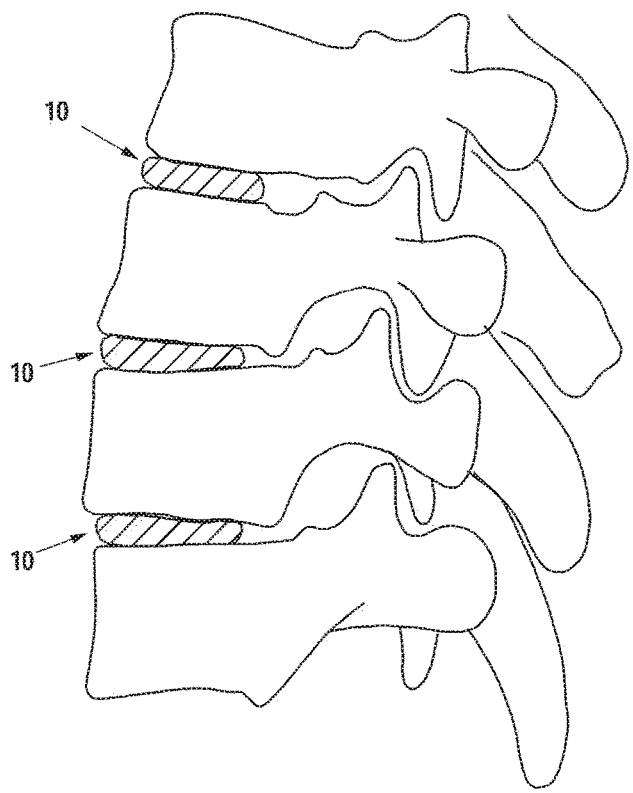
FIG. 20B is a sagittal, perspective view of the lumbar spine shown in 20A following restoration of the normal lumbar lordosis.

FIG. 20B demonstrates a potential minimally invasive surgical application of the present invention whereby prosthetic devices of the invention may be implanted at several levels possibly during a single minimally invasive procedure to restore normal lumbar lordosis.

I claim:

1. An inflatable prosthetic device for placement within at least a portion of an annulus fibrosus of a patient, said prosthetic device comprising:
    an annular balloon defining an annular lumen therein, said annular balloon comprising a first neck portion and a second neck portion;
    a tubular textile sleeve adjacent and receiving said annular balloon therein, said tubular textile sleeve comprising a first neck portion bonded to said first neck portion of said annular balloon and a second neck portion bonded to said second neck portion of said annular balloon;
    a securement implement bonded to said first neck portions and said second neck portions of said annular balloon and tubular textile sleeve to form a fluid tight connection;
    wherein said securement implement comprises a one-way valve, and a plurality of staples; and
    wherein said prosthetic device defines an interior space.

2. A method for attaching an annular prosthetic device to an outer margin of an annulus fibrosus, which comprises the steps of:
    retracting a tip of a delivery cannula to a level of the outer margin of the annulus fibrosus;
    retracting an access cannula to the level of the outer annulus; and
    applying forward pressure on a pusher implement, a disengagement implement, and an inflation cannula simultaneously to drive a tissue attachment ring towards the outer annulus margin and staple legs to firmly penetrate the annulus.

3. An intervertebral implantation system comprising:
    an inflatable prosthetic device comprising an annular component having an inner annular balloon defining an annular lumen therein and comprising a first neck portion and a second neck portion, an outer textile supporting sleeve adjacent said annular balloon comprising a first neck portion corresponding to the first neck portion of the annular balloon and a second neck portion corresponding to the second neck portion of the annular balloon;
    a securement element, disposed at a predefined location along the outer layer of said prosthetic device, and coupled to said first neck portion and said second neck portion of said annular balloon and said textile supporting sleeve;
    a fluid coupling assembly and a sealing valve assembly disposed within said securement element and in fluid-tight communication with said annular lumen;
    an attaching apparatus coupled to said securement element to attach said securement element to an outer margin of an annulus fibrosus of a patient;
    an access apparatus with an access cannula insertable therein,
    a delivery apparatus housing said prosthetic device in a contracted state, slidable within said access cannula to deploy said prosthetic device in a disc space of said patient.

4. The system of claim 3 further comprising a temporary high pressure balloon disposed within an interior space of said prosthetic device.

5. The system of claim 3 wherein said annular lumen expands said annular balloon radially and circumferentially upon inflation with a pressurized fluid.

6. The system of claim 3 wherein the first neck portion of the annular balloon is bonded to the second neck portion of the textile supporting sleeve, and the second neck portion of the annular balloon is bonded to the second neck portion of the textile supporting sleeve.

7. The system of claim 3 wherein said textile supporting sleeve is configured to provide differential compliance and constraint to prevent kinking and buckling of the annular component.

8. The system of claim 3 wherein said textile supporting sleeve provides differential compliance and constraint thereby effectuating distraction of adjacent spinal vertebrae to correct the coronal and sagittal plane of adjacent vertebrae.

9. The system of claim 3 wherein an in-situ curable liquid elastomeric material is injected into the annular balloon to inflate the annular lumen.

10. The system of claim 9, wherein the annular component, with said in-situ curable elastomeric material within said annular lumen, is elastomeric and isoelastic, providing dynamic mobility and stabilization to the vertebral segments.

11. The system of claim 3 wherein said annular lumen is in fluid-tight communication with said fluid coupling assembly and said sealing valve assembly of said securement element.

12. The system of claim 3 wherein the fluid coupling assembly comprises a detachable engagement mechanism adjacent a lumen of said inflation cannula, said engagement mechanism transferring fluid between said lumen of a removable inflation cannula and said annular lumen.

13. The system of claim 3 wherein the sealing valve assembly comprises a one-way valve to provide free flow of fluid from said inflation cannula to said annular lumen while preventing flow of fluid in the opposite direction.

14. The system of claim 3 wherein said attaching apparatus comprises more than one penetrating pin for attaching said securement element and the annular component coupled thereto to the outer margin of the annulus fibrosus.

15. The system of claim 3, wherein the textile support sleeve is a porous polymeric structure formed from fibers that are configured in woven, braided, knitted, or electrospun configurations and to impart semi compliance, strength, flexibility, and kink resistance to prosthetic device.

16. The system of claim 3, wherein said annular balloon is formed from a compliant polymeric material capable of an elongation ratio of 5:1.

17. The system of claim 3, wherein said annular balloon is formed from a semi-compliant polymeric material capable of differential expansion without kinking or buckling.

18. The system of claim 3, wherein said annular balloon is formed from a noncompliant polymeric material capable of differential expansion without kinking or buckling.

19. The system of claim 3, wherein said delivery apparatus comprises;
    a rigid cannula body having a distal end and a proximal end with a lumen extending there between, the distal end including a loading portion.

20. The system of claim 17 wherein said annular prosthetic device is compressed and disposed within said loading portion of said delivery apparatus.

21. The system of claim 20 wherein said inflation cannula comprises a proximal end connected to a source of pressurized fluid and a distal end detachably coupled to said fluid coupling assembly in a fluid-tight engagement.

22. The system of claim 21 wherein said delivery apparatus comprises a disengagement implement configured to provide controlled detachment of said inflation cannula and a pusher implement to forcibly advance a tissue attachment ring of the attachment apparatus and staple legs into the outer margin of the annulus fibrosus.

* * * * *